United States Patent
Rodriguez et al.

[11] Patent Number: 5,125,737
[45] Date of Patent: Jun. 30, 1992

[54] MULTI-PART DIFFERENTIAL ANALYZING APPARATUS UTILIZING LIGHT SCATTER TECHNIQUES

[75] Inventors: Carlos M. Rodriguez, Miami; Wallace H. Coulter, Miami Springs, both of Fla.

[73] Assignee: Coulter Electronics, Inc., Hialeah, Fla.

[21] Appl. No.: 479,199

[22] Filed: Feb. 13, 1990

Related U.S. Application Data

[63] Continuation of Ser. No. 129,954, Dec. 4, 1987, abandoned, which is a continuation-in-part of Ser. No. 25,442, Mar. 13, 1987, abandoned.

[51] Int. Cl.$^5$ .............................................. G01N 33/49
[52] U.S. Cl. ........................................ 365/39; 356/72; 356/338
[58] Field of Search ................... 356/39, 72, 73, 336, 356/338, 343

[56] References Cited

U.S. PATENT DOCUMENTS

| | | | |
|---|---|---|---|
| 2,656,508 | 10/1953 | Coulter | 324/71 |
| 3,502,973 | 3/1970 | Coulter et al. | 324/71 |
| 3,502,974 | 3/1970 | Coulter et al. | 324/71 |
| 3,596,035 | 6/1986 | Gershman et al. | 382/6 |
| 3,705,771 | 12/1979 | Friedman et al. | 356/343 |
| 3,730,569 | 8/1974 | Meric | 356/39 |
| 3,883,247 | 5/1975 | Adams | 356/39 |
| 4,178,103 | 12/1979 | Wallace | 356/336 |
| 4,274,741 | 6/1981 | Cornillault | 356/336 |
| 4,284,412 | 8/1981 | Hansen et al. | 356/39 |
| 4,298,836 | 11/1981 | Groves et al. | 324/71 |
| 4,348,107 | 9/1982 | Leif | 356/72 |
| 4,420,720 | 12/1983 | Newton et al. | 324/71.4 |
| 4,515,274 | 5/1985 | Hollinger et al. | 209/3.1 |
| 4,527,114 | 7/1985 | Coulter | 324/71.1 |
| 4,702,598 | 10/1987 | Böhmer | 356/73 |
| 4,735,504 | 4/1988 | Tycko | 356/336 |

FOREIGN PATENT DOCUMENTS

| | | | |
|---|---|---|---|
| 1125050 | 6/1982 | Canada | 356/338 |
| PCT/US85/-00868 | 9/1985 | PCT Int'l Appl. | |

OTHER PUBLICATIONS

M. Bartholdi et al., Differential Light Scattering Photometer for Rapid Analysis . . . ; Applied Optics, 15 May 1980, vol. 19, No. 10, pp. 1573–1581.

G. C. Salzman et al.; Cell Classification by Laser Light Scattering: Identification and . . . ; Acta Cytologica, vol. 19, No. 4 (1975) pp. 374–377.

Scientists Study Sorting of Human Cells; 167th National ACS Meeting; C&EN, Apr. 15, 1974, pp. 11–12.

G. C. Salzman et al.; A Flow-System Multiangle Light-Scattering Instrument . . . ; Clinical Chemistry, vol. 21, No. 9 (1975) pp. 1297–1304.

R. A. Thomas et al.; Combined Optical and Electronics Analysis of Cells . . . ; The Journal of Histochemistry and Cytochemistry, vol. 25, No. 7, pp. 827–835, 1977.

H. B. Steen; Simultaneous Separate Detection of Low Angle and Large Angle Light Scattering in an Arc Lamp-Based . . . ; Cytometry 7:445–449 (1986).

*Primary Examiner*—Richard A. Rosenberger
*Attorney, Agent, or Firm*—Carl Fissell, Jr.; Gerald R. Hibnick

[57] ABSTRACT

Disclosed is a flow through particle analyzing cell differentiating apparatus for optical and electronic measurements on a stream of particles in which a hydrodynamically focoussed stream is passed into and through a point focussed beam of radiated energy whereby the beam is scattered by the stream to impinge upon light responsive signal operating members disposed adjacent the cell at angular positions relative to the beam axis of from about 10° to 70°.

40 Claims, 11 Drawing Sheets

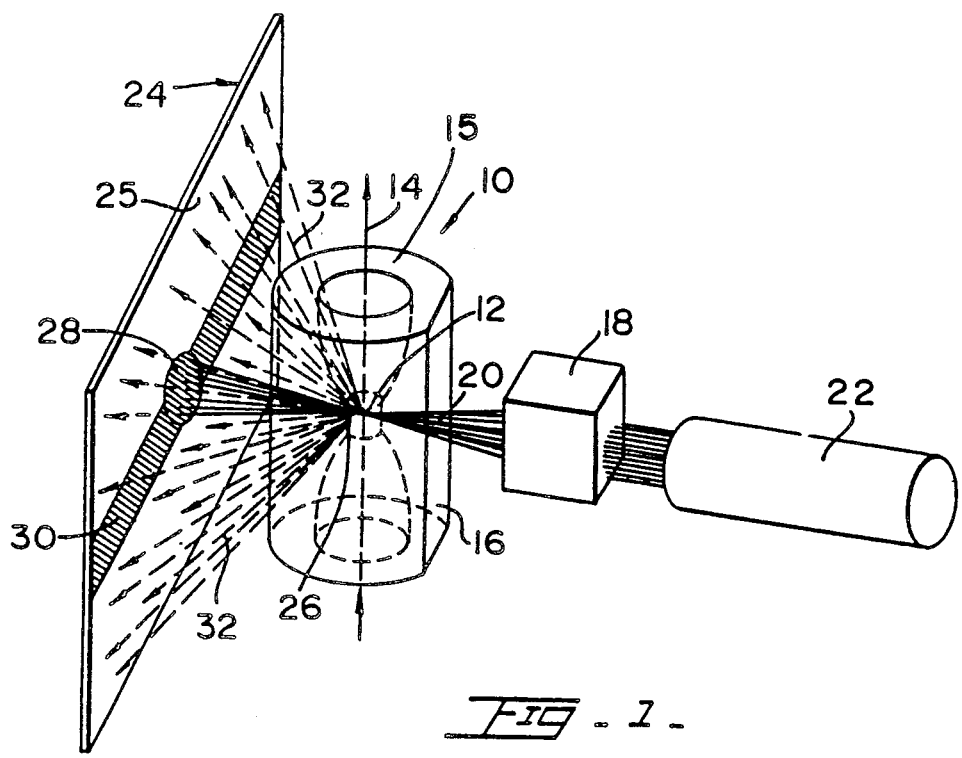
FIG - 1 -
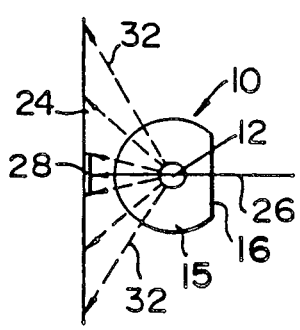
FIG - 1A -
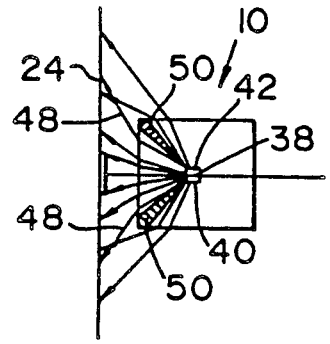
FIG - 1B -
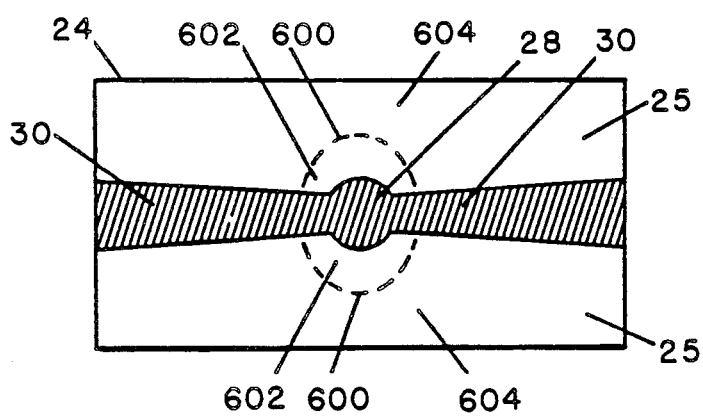
FIG - 1C -

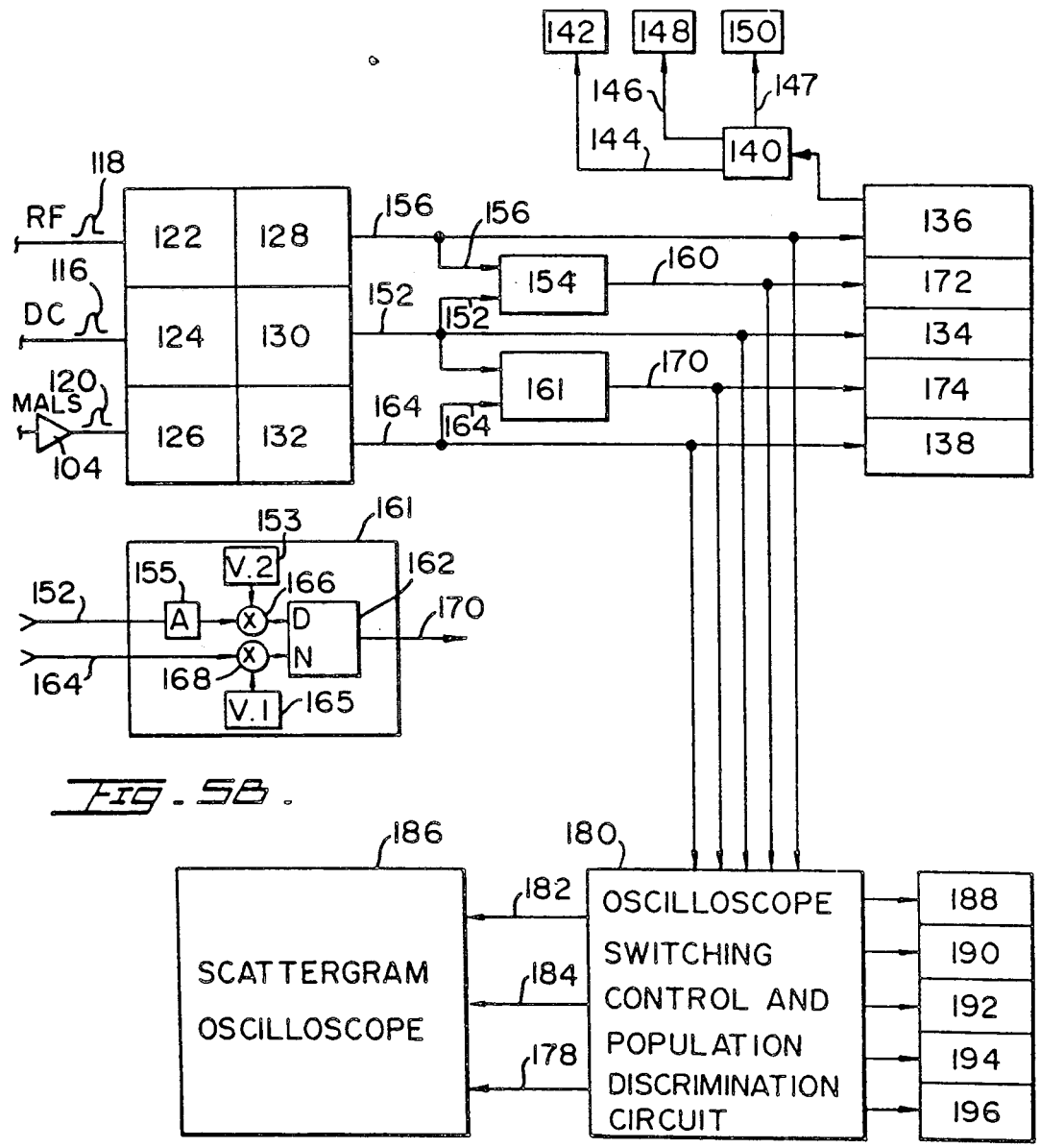

MULTI-PART DIFFERENTIAL ANALYZING APPARATUS UTILIZING LIGHT SCATTER TECHNIQUES

This is a continuation of co-pending application Ser. No. 07/129,954 filed on Dec. 4, 1987, now abandoned, which is a continuation-in-part of co-pending application Ser. No. 07/025,442 filed on Mar. 13, 1987, now abandoned.

BACKGROUND OF THE INVENTION

1. Field of the Invention

The present invention relates generally to particle analyzing apparatus and more particularly to apparatus and method for achieving selective, discriminate, differential classification of individual blood cell types, for example, five basic types of leukocytes, by means of technology of the Coulter type without the utilization of cytochemical staining techniques or materials.

2. Description of the Prior Art

It is well known that leukocytes can be discriminated and classified into three main types, lymphocytes, monocytes, and granulocytes, by means of flow cytometry instrumentation and without the use of cytochemical staining. One such method involves using low angle light scatter in combination with 90° or high angle light scatter. Some methodologies use a lysing reagent to remove unwanted erythrocytes from a whole blood dilution; others rely on density or centrifugation techniques, such as, ficol, dextran, "buffycoat", etc. In addition, some methodologies use cytochemical staining in order to further subclassify lymphocyte subsets, as defined by immunological function.

PCT/US85/00868 to S.L. Ledis and H.R. Crews, assigned to Coulter Electronics, Inc., Hialeah, Florida, describes a system and techniques for producing what is characterized as a four population differential by utilizing a reagent system in such a way that the erythrocytes or red cells are effectively removed from the sample and, due to the lysing and if necessary fixing process, a granulocyte subpopulation, namely eosinophils, is separated out, in contrast to the earlier described techniques wherein only three populations are made visible or apparent, the eosinophils then being undistinguishable from the other subpopulations.

The prior art describes a method and means for obtaining a four-part leukocyte differential—lymphocytes, monocytes, neutrophils, and eosinophils—by cytochemically staining the cells to yield four distinct groups by the combination of low angle light scatter and absorption. Absorption is a component of axial light loss.

Also, in a technique in which electrical "opacity", as taught in U.S. Pat. No. 3,502,974, is plotted as a separate parameter for detecting certain cells or clusters of cells, the three populations are once again differentiated and fairly well defined and separated. However, in this instance, the granulocyte subpopulations of neutrophils, eosinophils, and basophils, are within the granulocyte cluster data, which hides or masks these three from differentiation.

The prior art literature, scientific papers and reports, illustrate, describe, and discuss the use of light scatter techniques at a variety of angular positions relative to the axis of the light beam being utilized to illuminate and interrogate the sample. However, the majority of the literature material so far available and considered restricts the light intersecting angles to either 0° to 23° or 90°, or both relative to the light axis.

SUMMARY OF THE INVENTION

The present invention provides a new, useful, and heretofore unobvious biological cell counting, measuring, and differentiating method and apparatus for use in high speed, accurate analysis and separation of cell types from each other within biological cell samples.

Broadly, the present invention provides a structural combination in which a biological sample, in the form of a hydrodynamically focused stream of particles, is passed into and through a point focused beam of the electromagnetic radiated energy, laser light. Light responsive means, suitably positioned with respect to the axis of the laser energy, provides a light output pulse indicative of the passage of each cell. Electrically conductive contacts within the fluid stream pathway provide additional electrical pulse outputs as the result of Coulter DC volume and RF/DC Coulter opacity interrogation of each cell.

By means of suitable electronic circuitry these output pulses or signals can be combined to define at least five different types of leukocytes, effectively distinguishing one cell type from another, even though certain statistically less common cell subpopulations may, in fact, be masked or hidden by their generic cell type.

The present invention also has to do with apparatus and method for generating data representative of one or more of multiple biological cell types for example, eosinophils by means of light scattering techniques alone and in combination with DC and RF technology of the Coulter type as a result of the inherent, natural characteristics of the whole blood cells and not as a result of a treatment for specifically altering the characteristics of the whole blood cells for differentiating eosinophils.

Still more specifically, novel apparatus and methodology is provided by the present invention for utilizing the information or data derived from a light responsive pulse generating assembly which is arranged in the output area of a masked laser beam at a range of angles relative to the laser axis of from about 10° to about 70°, characterized hereinafter as median angle light scatter or MALS.

CROSS REFERENCE TO RELATED APPLICATIONS

The present application is related to the following listed patents and/or applications and incorporates, by reference to the same, those teachings which the present application relies upon for additional explanatory details, where such is thought to be necessary or required. "Method and Reagent System for Isolation, Identification and/or Analysis of Leukocytes from Whole Blood Samples", U.S. patent application Ser. No. 07/025,303, filed Mar. 13, 1987, to Stephen L. Ledis et al., assigned to the Assignee of the present application. Copending U.S. patent application Ser. No. 07/025,337, filed Mar. 13, 1987, to Wallace H. Coulter et al., entitled "Method and Apparatus for Rapid Mixing of Small Volumes for Enhancing Biological Reactions". U.S. patent application Ser. No. 06/921,654, filed Oct. 21, 1986, to Wallace H. Coulter et al., entitled "Particle Analyzer for Measuring the Resistance and Reactance of a Particle", and assigned to the Assignee of the present application.

Since its conception in the early 1950's the principle of particle counting and sizing invented by Wallace H.

Coulter has resulted in numerous methods and flow-through apparatuses for the electronic counting, sizing, studying, and analysis of microscopic particles, which are scanned in a fluid suspension, as shown by the pioneer U.S. Pat. No. 2,656,508 to Coulter. In this prior art arrangement, a DC electric current flow is established between two vessels or chambers by suspending electrodes in the respective bodies or cavities of the suspension fluid. The only fluid connection between the two bodies is through an aperture; hence, an electric current flow and field are established in the aperture. The aperture and the resultant electric field in and around it constitute a sensing zone. As each particle passes through the sensing zone, for the duration of the passage, the impedance of the contents of the sensing zone will change, thereby modulating the current flow and electric field in the sensing zone, and causing the generaton of a signal to be applied to a detector suitably arranged to respond to such change.

U.S. Pat. No. 3,502,974 to W.H. Coulter and W.R. Hogg, assigned to Coulter Electronics, Inc., Hialeah, Fla., describes particle analysis apparatus for responding to the passage of fluid suspended particles through a microscopic path by generating and detecting signals as a result of such passage. The signals are related to electric current changes caused in the path due to the passage of the particles, and these changes primarily comprise resistive and reactive current components which reflect physical characteristics of the particles. The current in the path is provided by current excitation means of at least radio frequency and preferably in combination with another different frequency; however, any two different frequencies are adequate so that the signals are separable from one another because of their location in the frequency spectrum and/or their phase relationship. At least two resulting signals are derived for each particle and are capable of being used to ascertain more than one physical characteristic of each particle, so that even particles of identical size but of different substance would be separately detectable.

U.S. Pat. No. 3,502,973 to W.H. Coulter and W.R. Hogg, (a continuation-in-part of U.S. Pat. No. 3,502,974) assigned to Coulter Electronics, Inc., Hialeah, Fla., describes apparatus in which there are two channels for receiving trains of pulses from a prior particle analyzing device of the Coulter type, each pulse normally having a companion pulse produced in the particle analyzing device by the same particle, and means are provided for achieving a signal which represents the relationship between pulses. In several embodiments, one pulse is attenuated in accordance with a particular factor and then compared with the other in a threshold circuit, so that only pulses of a certain range will produce output signals. In other embodiments, electronic windows are formed by means of pairs of thresholds, and one signal of each pair is treated by attenuation in two attenuators to provide two signals defining a given range. Only relationships which fall within the range result in output signals.

U.S. Pat. No. 4,527,114 to Wallace H. Coulter, assigned to Coulter Electronics, Inc., Hialeah, Fla., describes a particle analyzer apparatus comprising a flow cell having a flow chamber wherein a flow of liquid suspension, having individual particles entrained therein, proceeds along a predetermined path; a pair of electrodes are disposed on opposed sides of the predetermined path, one of the electrodes having an end with a width parallel to the predetermined path that is less than the length of a given particle, the end of the electrode being positioned in close proximity to the predetermined path; energizing source for providing an electrical field between the pair of electrodes that traverses the predetermined path; and a particle pulse detector for detecting particle pulses caused by the particles passing through the electric field.

U.S. Pat. No. 4,298,836 to Michael R. Groves and Wallace H. Coulter, assigned to Coulter Electronics, Inc., Hialeah, Fla., describes apparatus and method wherein particles in a liquid stream are hydrodynamically focused to pass through an impedance sensing orifice, a low frequency current source provides a current through the orifice to produce a signal representative of the particle's size, a high frequency source provides a current through the orifice to produce a signal representative of the particle's size and internal resistance, a detector determines the particle's length, and a digital computer correlates the signals for each particle and calculates its shape factor, degree of deformation or natural shape, true volume and internal resistivity.

U.S. Pat. No. 4,420,720 to William A. Newton and Marshall D. Graham, assigned to Coulter Electronics, Inc., Hialeah, Fla., describes a particle analyzer wherein a flow of liquid suspension, having individually entrained particles, flows along a predetermined path; a center pair of electrodes are positioned on opposed sides of the predetermined path; the center electrodes are energized to provide an electrical sensing field therebetween, two pairs of outer electrodes are positioned so that one pair is on each side of the center electrodes; the outer electrodes are oriented and/or energized so that their electrical fields bulge outward in the direction of the sensing field of the center plates to narrow the width of the sensing field along the predetermined path. Additionally, the field between the center plates can be focused in additional directions and the sensing electrode arrangement can be implemented in a flow cell, with or without an aperture, or on the surface of a substrate.

U.S. Pat. No. 4,515,274 to John D. Hollinger and Raul 1. Pedroso, assigned to Coulter Electronics, Inc., Hialeah, Fla., describes a flow-through particle analyzer and sorter apparatus for simultaneous optical and electrical impedance measurements on a stream of particles, comprising a flow cell having a pair of channels fluidly connected by a particle sensing aperture, through which the particles pass and are analyzed; a nozzle mounted at the end of the downstream channel so as to define a flow chamber; a sheath liquid which is introduced at the bottom of the flow chamber to hydrodynamically focus the particle stream and to jet the same in a liquid jet from the nozzle; and a system for creating droplets from the liquid jet and for thereafter sorting the droplets.

U.S. Pat. No. 4,348,107 to Robert C. Leif, assigned to Coulter Electronics, Inc., Hialeah, Fla., describes an electro-optical transducer for simultaneously making optical measurements and electrical volume measurements on particle suspended in a flow stream passing through an orifice positioned inside an optically clear spherical element.

BRIEF DESCRIPTION OF THE DRAWINGS

FIG. 1 is an idealized rendering of a flow cell and operably associated hardware including photo detector assembly embodying the present invention;

FIG. 1A is a top plan view of the flow cell of FIG. 1 cut horizontally across the aperture plane;

FIG. 1B is a top plan view of a flow cell embodying a square quartz aperture with flat internal and external surfaces;

FIG. 1C is a front view of the photodetector assembly, illustrating the signal reception areas;

FIGS. 5, 5A, and 5B taken together constitute a block diagram of an operational electronic circuit and apparatus for implementing the present invention utilizing a Coulter volume aperture;

DESCRIPTION OF THE PREFERRED EMBODIMENT DEFINITIONS

Figure 2:
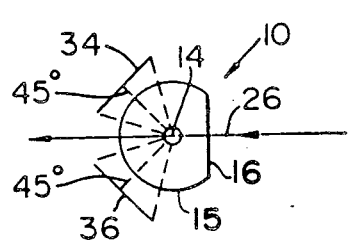
FIG. 2 is a top plan view of the flow cell of FIG. 1 cut horizontally at the aperture, with two 45° angled photodetector assemblies.

"Histogram" is defined to be a graph of frequency distribution for a single variable, displayed as a two dimensional line graph with the variable plotted on the X axis and the frequency, designated as "#", plotted on the Y axis. Histogram also is defined as the abstract numerical tabulation of such a graph as represented within a computer or some other form of electrical circuit.

"Matrix" is defined to be a graph of frequency distribution for two independent variables, displayed as a three dimensional contour graph with one variable plotted on the X axis, the second variable plotted on the Y axis, and frequency or count displayed as iso-count contours. For clarity, only one iso-count contour will be displayed to show population outlines. Matrix also is defined as the abstract numerical tabulation of such a graph as represented within a computer or some other form of electrical circuit. When describing a matrix in this Specification, the X axis variable will be listed first, followed by the Y axis variable.

"Parameter" is synonymous with independent variable and, in this invention as set forth in the following Specification, refers to any of the simultaneous, independent measurements obtained from particles or cells being analyzed in a flow cytometer. The combination of two or more parameters, by some mathematical function, is defined as yielding another parameter.

"Gating" is defined as a filtering process used in constructing, from multi-parameter data, a histogram of one parameter, while interrogating one or more of the other parameters. For each event, which is the passage of a single white blood cell through the flow cell and the generation of cell measurements by the parameter transducers, the value or measurement corresponding to each parameter that is to be used for gating is compared with one or two reference values, or thresholds, and "tested" for being below the threshold, above the threshold, or between the two thresholds. If this test yields a true result for all the gating parameters being considered, then the event is included in the histogram. Gating also can be used to construct a matrix. Thus, by using gating, it is possible to simplify the analysis and graphic representation of multi-parameter data.

"Low angle light scatter", LALS is defined as that light scatter information obtained below 10° relative to the laser beam axis, excluding 0°. "High angle light scatter", HALS is defined as that light scatter information centered at 90° to the laser axis. "Median angle light scatter", MALS is defined as that light scatter information obtained at angles between 10° and 70°.

"Beam dump" is defined as an obstruction for removing unwanted laser light, which generally appears as a horizontal line across the light detector as a result of the interaction between the laser beam and the flow cell, which degrades the detected light scatter signal.

"Mask" is defined as a circular or elliptical obstruction that removes unwanted low angle light scatter information, as well as 0°, or on-axis laser light information, and prevents reception of this information by the light detector.

In the following paragraph, and throughout this description, light scatter angles are defined as the angles of the light exiting the biological cell within an aperture or sensing zone, still to be described. The angles of the scattered light striking a photodetector assembly, to be described shortly, can differ from the true angles within the aperture due to differences in indices of refraction of sample diluent, and/or hydrodynamic sheath flow fluid, air, and the flow cell material, and also due to the architecture of the flow cell 10, as predicted by Snell's Law.

FIG. 1 illustrates a type of particle analyzing apparatus employing the method and process of the present invention. The apparatus of FIG. 1 is seen to comprise an elongated, cylindrical member, characterized as a flow cell 10. Flow cell 10 can be of any optically transparent material, for example, fused silica, quartz, or sapphire. The interior portion of the flow cell member 10 is cylindrical throughout its length, except for a narrowed or necked-down aperture 12 through which a biological cell sample is passed or flowed as a hydrodynamically focused stream 14 by well known means, not shown in this figure. The exterior wall surface 15 of member 10 is cylindrical and includes an optical flat 16 for purposes which will become more apparent as the description proceeds. A lens system 18 focuses a beam 20 of electromagnetic light energy, preferably from a laser 22, into a spot at the aperture 12. The laser, in a preferred embodiment, is a helium-neon laser which emits at 632.8 nm. Lasers emitting at other wave lengths, for example, 488 nm, can be used, yielding similar results to those described hereinafter. A photodetector assembly structure 24, acting as a scattered radiation receptor, is positioned in a plane orthogonal to the axis 26 of the laser radiated light and centered on the axis 26.

The photodetector assembly 24 is comprised of a photodetector 25 with a mask 28 and a beam dump 30, as earlier defined herein. The photodetector 25 can be any type of photosensitive electrical device, for example, a photomultiplier tube. In this embodiment, the photodetector 25 is a silicon photovoltaic detector, part number VTS3081, manufactured by Vactec, Inc.

The central portion of the photodetector assembly 24 is, as before mentioned, provided with a light scatter mask 28. The mask 28 can be of a circular, elliptical, or other shape, as required to obtain equivalent light scattering information from flow cells 10 of different architectures, as described previously. The mask 28 is oriented coaxial with the laser light beam 20. The so-called beam dump 30 extends horizontally across the photodiode assembly 24 facing the laser beam as shown. The beam dump 30 can be slightly angularly fanned out from the center axis as shown hereinafter, so as to provide a cleaner signal to noise output.

FIG. 1A is a top plan view of the flow cell 10 of FIG. 1, cut horizontally across the aperture plane. The photodetector assembly 24 is shown with the mask 28 centered with the laser light beam axis 26. The beam dump 30 is not shown in this figure.

The light exiting from the rear side, left in FIG. 1, of the aperture 12, after interrogating or striking a cell in the stream 14, is caused to fan out into a funnel-shape, which is characterized as "light scatter" 32. The angular orientation of the mask 28 and the beam dump 30 is such that the light scatter output 32 generally can be received through a 60° angular range relative to the laser axis, 40°±30° or from approximately 10° through approximately 70°. There is thus provided a range of angles centered about 40° from the laser beam axis 26, which is taken to be 0°, in the forward direction, leftward in FIG. 1. This optical arrangement offers a collection range of ±30°, which in turn provides an annulus of approximately 10° to 70° from the laser beam axis.

It should be clear from the foregoing description that the present invention utilizes a substantially flat, planar photodetector structure or assembly 24 which, as shown, is positioned in front of the flow cell, transducer, 10. The assembly 24 is provided with the round or circular mask 28 in order to remove or block the low angle light scatter, which is lower than 10°, as earlier described. In addition, for practical construction purposes, the horizontal beam dump 30 is coupled to the mask 28. The latter may take the form of a bow tie, being larger or wider at the outer ends thereof than at the center. The horizontal beam dump 30 is employed to accommodate the optics to the condition wherein the laser beam is shaped so as to be stretched or flattened in the horizontal direction to make the system less sensitive to cell or particle position, as the cells or particles flow through the cell chamber 10. This optical shaping thus provides a more uniform light output signal for use in electronically utilizing the light scatter signal output.

FIG. 1C is a front view of the photodetector assembly 24 shown on FIG. 1. Shown on FIG. 1C are the circular mask 28, beam dump 30, and the exposed surface of the photodetector 25, which provides the median angle light scatter signal, hereinafter referred to as the MALS. Additional items not on FIG. 1 are a dashed line 600, which divides the MALS into two regions of angular information 602 and 604. The dashed line 600 denotes the locations where light scattered at 20° would hit the surface of the photodetector 25. The dashed line 600, which can be represented as a circle or as a parabola, depending on the geometry of the flow cell 10 and other factors explained earlier, maps onto the photodetector 25 surface as a parabola, as shown in FIG. 1C, when using the flow cell 10 described as the preferred embodiment, which has a cylindrical aperture 12 and cylindrical outer surface 15 in the direction in which MALS is received.

The region 602 between the mask 28 and the dashed line 600 receives light scattered within the angles of 10° and 20°. This region 602 will be called "15° LS", hereinafter referred to as "Lower Median Angle Light Scatter", LMALS, throughout this document. The region 604 delimited by the dashed line 600 and the outer edges of the photodetector 25 receives light scattered within the angles of 20° and 65°, which will be called hereinafter "Upper Median Angle Light Scatter", UMALS.

For this description, blood cells are assumed to be passing, one by one, through the aperture 12 of the flow cell 10 shown in FIG. 1. A complete system description, which details how blood cells or other particles are introduced into flow cell 10, and how multi-parameter data on said cells is obtained and processed in order to achieve classification, will be provided hereinafter. Leukocytes, in a substantially native state, traversing the aperture 12, will scatter light in the median angle range of 10° to 70°, as described previously. Eosinophils will scatter more light than neutrophils in the upper median angle light scatter range, UMALS, region 604 in FIG. 1C. Neutrophils will scatter more light than lymphocytes, basophils, and monocytes in the upper region 604. In the lower median angle light scatter range, LMALS, denoted as region 602, eosinophils and neutrophils will scatter about the same amount of light, making eosiniphils indistinguishable from neutrophils. The amount of light scattered by neutrophils relative to the amount of light scattered by lymphocytes, basophils, and monocytes is much greater in the LMALS region 602 than in the UMALS region 604. Combining the lower region 602 with the upper region 604 into a single measurement, median angle light scatter, MALS, yields a measurement that provides maximum differentiation between three groups, in decreasing order of light scatter signal amplitude: eosinophils; neutrophils; and lymphocytes, basophils, and monocytes.

Since the results produced by the UMALS subset of the full MALS are similar throughout the rest of this document, reference to median angle light scatter, or MALS, can refer to the full MALS measurement or its upper UMALS subset. Rotated light scatter, RLS, to be described hereinafter, similarly can be computed using the full MALS or UMALS. Treating leukocytes with a lysing agent, to be described later, it is possible to differentiate eosinophils from neutrophils by the amplitudes of their LMALS signals. The relationship between the various aforementioned cell types on UMALS is virtually unchanged.

The present invention lends itself to certain readily constructed permutations and combinations. One such modified form of the inventive apparatus is that illustrated in FIG. 1B of the drawings. In this embodiment, a "square" quartz aperture 38, having flat internal surfaces 40 and 42, is provided. The photodetector assembly 24 is positioned as illustrated in FIG. 1B and its construction is similar to the detector assembly 24 in FIG. 1. Since the indices of refraction of quartz, air, and sample fluids, etc., are different, there will be a bending of the light, as predicted by Snell's Law. In this instance, the light rays 48 exiting from the rear of the flow cell, left in FIG. 1B, are bent towards a high angle relative to the beam axis with a small dead spot 50, due to the interference at the corners of the flow cell 10. All other angles of interest with respect to particle and cell enumeration and classification, no matter how the angles criss-cross on the surface of detector 24, are collected.

In another embodiment, FIG. 2 shows a top view similar to FIG. 1A of the flow cell 10 shown in FIG. 1 and described previously. One or two photodetector assemblies 34, 36 can be positioned orthogonal to a line at 45° from the laser axis 26, in the forward direction, and parallel to the axis of the sample stream 14. The output signals from sensors 34, 36 would be added in the electronic control circuitry in order to increase the signal to noise ratio.

Figure 2A:
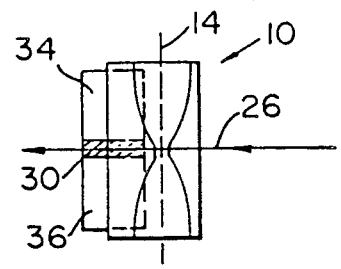
FIG. 2A is an enlarged side elevational view of the aperture portion of the device of FIG. 2 (not to scale)

FIG. 2A shows a side view of the flow cell 10 of FIG. 2 and the position of the photodetector assemblies 34 and 36. The cross hatched area is the masked out portion due to the beam dump 30 for the horizontal pattern of laser light generated by the combination of the beam shaping optics 18 and the flow cell 10.

Figure 3:
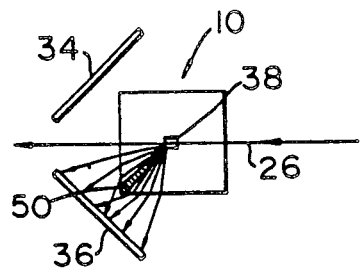
FIG. 3 is a top plan view (not to scale) of a modified version of the device of FIG. 1B.

The embodiment of FIG. 3 illustrates a still further variant of the basic concept of the present invention. In this case, a flow cell 10, with the "square" aperture shown in FIG. 1B, is combined with one or two of the photodetector assemblies 34, 36 of FIG. 2. The light rays will experience bending, as described previously, but the light scattering information obtained with this embodiment is effectively the same as that obtained with the embodiment illustrated in FIG. 2.

Figure 4:
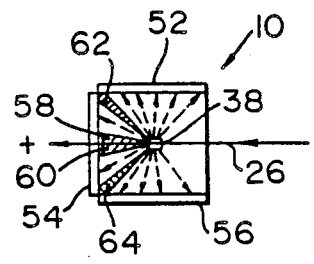
FIG. 4 is a top plan view of a still further modified version of the apparatus of FIG. 1B.

Another embodiment of the present invention is shown in FIG. 4 of the drawings. In this construction, photodiode sensors 52, 54, and 56 are placed at the sides and front of the square aperture 38. A circular mask 58 is positioned in front of the front photodiode 54 to block out the lower 10° of laser light scatter, leaving the dark area 60 as a result. Again, as with the construction of FIG. 3, due to Snell's Law, dark areas 62 and 64 exist at the corners on each side of the laser axis. A horizontal beam dump, not seen in FIG. 4, similar to dump 30 in FIGS. 1 and 2, is used on all photodiode sensors 52, 54, and 56.

In addition to MALS, the present invention is capable of utilizing at least seven other parameters: DC, RF, opacity, RLS, NALS, ALL, and 15° LS, which is a subset of MALS.

DC and RF refer to the Coulter Principle of aperture impedance cell sensing. DC is defined as the pulse peak information obtained from applying a direct or low-frequency current, such that the cell membrane is not penetrated and no current flows through the cell. The peak amplitude of the DC pulse is a function of cell volume. RF is defined as the pulse peak information derived from the measurement obtained from applying a high-frequency current, such that the cell membrane is short-circuited and current flows through the cell. RF is a function of cell volume and internal conductivity. "Opacity" is defined as the signal value or data obtained by the division of the RF signal data by the DC signal data, for every individual cell measurement or event, yielding a new cellular parameter which is independent of size, but is a function of internal conductivity.

RLS, rotated light scatter, is defined as a function whereby the pulse peak information derived from the logarithm of MALS, plus a constant, is divided by DC, as before defined, plus a constant. A detailed example of a circuit for providing RLS is described elsewhere in this Specification. This RLS function has the effect of removing size component, yielding a measurement which is more related to internal structure. An alternative method for obtaining RLS consists of dividing the logarithm of MALS signal data by the logarithm of the DC signal data.

NALS, narrow angle light scatter, which is a subset of LALS, low angle light scatter, is well defined in the literature as a range of angles from 0.5° to 2° from the laser beam axis, in the forward direction. ALL, axial light loss, is a signal obtained by placing a photodetector in line with the laser beam after it exits the flow cell 10, and passes through a small aperture which is sized to accept only the laser beam and thereafter amplifying the change in amplitude of the signal due to the passage of a particle or cell through the sensing zone 12. Both NALS and ALL are influenced strongly by cell size and, thus, can be used as alternatives to DC. 15° LS is defined as a subset of MALS obtained by allowing only light onto a photodetector in an annular range at 15° from the laser beam axis, and with an acceptance angle of ±5, yielding an annulus of from 10° to 20° about the laser beam axis. Embodiments using NALS, ALL, and 15° LS are described elsewhere in this Specification.

Utilizing "native", non-dyed white blood cells, it is possible, with the hardware earlier described, to produce the histograms of FIGS. 7 to 27 in which the various cell clusters or populations appear as generally separate clusters as shown. Parameters 1 and 2 in combination are used to produce the RLS parameter. As illustrated, lymphocytes, monocytes, neutrophils, eosinophils, and basophils are displayed as separate clusters.

Each of the eight parameters is discussed more or less in detail hereinafter with respect to the individual figure or figures then under consideration.

Figure 5:
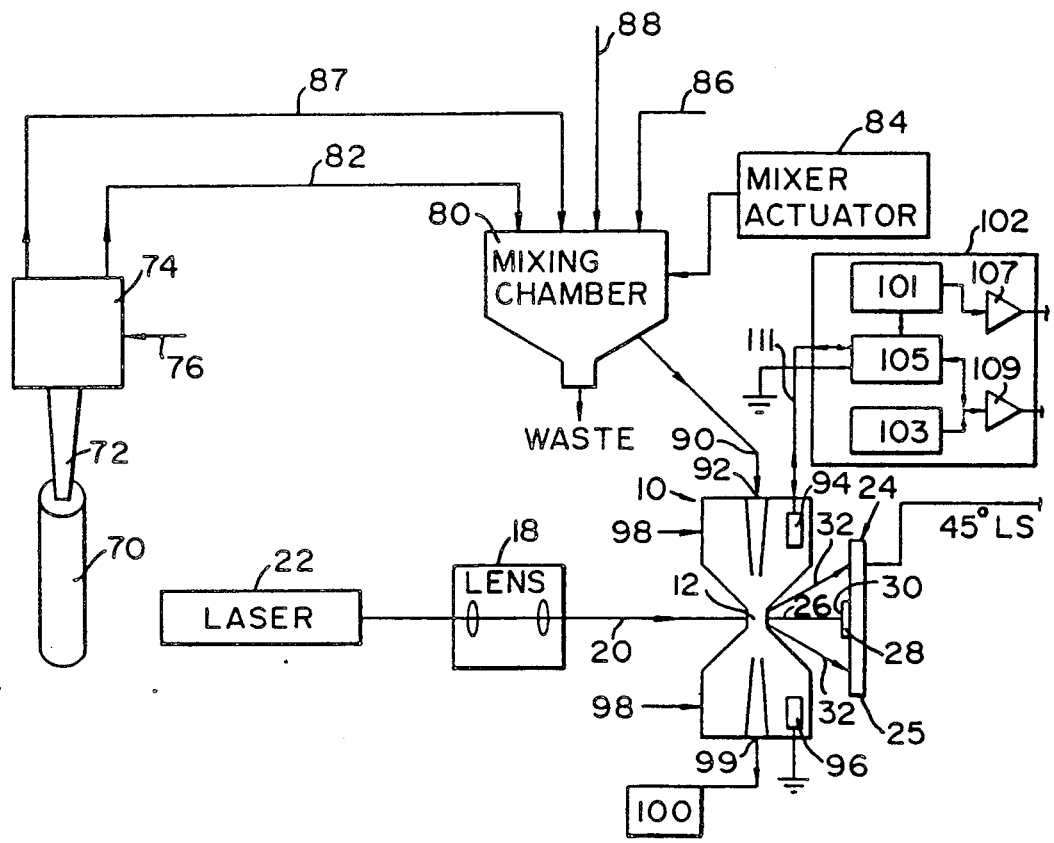

Fluidic and electrical control circuitry for the present invention is set forth in the block diagram of FIG. 5. In the diagram, there is shown a sample container 70 which can be a test tube, a cuvette, or other suitable similar means for holding a quantity of material to be examined in this example "native" or non-cytochemically treated or stained leukocytes. In the present instance, the flow cell 10 is supplied through an aspirator needle 72 with a fixed quantity of whole blood by means of a standard Coulter Electronics, Inc. sampling valve 74. Approximately twenty-eight microliters of sample is push-mixed with a lysing agent 76 from a reagent package section 78 to a mixing chamber 80 via a conduit 82. In the mixing chamber 80, the whole blood cell sample and lyse are shaken-mixed for approximately five to six seconds under the control of a mixer actuator 84, such as described and illustrated in copending U.S. patent application Ser. No. 07/025,337, filed Mar. 13, 1987, to Wallace H. Coulter et al., entitled "Method and Apparatus for Rapid Mixing of Small Volumes for Enhancing Biological Reactions". The mixing strength is controlled by adjusting the frequency and duty cycle of the actuator. After five to six seconds, a quench liquid 86 is added to the mixed and lysed sample and the mixing is continued for another five to six seconds. The resulting sample is now considered to be prepared. The term "resulting" is used herein to call attention to the fact that the lysing reagent 76 has hemolyzed the red cells and platelets, leaving substantially "native" the white cell subpopulations. The term "prepared" is used herein to call attention to the fact that the quench liquid 86 has terminated the lysing activity and otherwise conditioned the white cells and their suspending media for subsequent analysis. The formulas and details of the lyse and quench are set forth in copending U.S. patent application Ser. No. 07/025,303, filed Mar. 13, 1987, to Stephen L. Ledis et al., entitled "Method and Reagent System for Isolation, Identification and/or Analysis of Leukocytes from Whole Blood Samples", and assigned to the Assignee of the present application, Coulter Electronics, Inc. Alternatively, as shown in FIG. 5, there is provided means for utilizing a so-called "pre-prep" mode of operation. In this mode, there is provided a purified white cell sample, for example, by centrifugation, density, or buffy coating technique, whereby the sample is devoid of red cells. The sample is aspirated as before, but is passed through a pre-prep line 87 to the mixing chamber 80, after which it is introduced into the cell flow chamber 10. From this, it is readily apparent that the system requires no lyse, quench, nor any reagent treatment to obtain the output results desired. The mixing then is stopped and the mixing chamber 80 is pressurized from a fluidics and pneumatics supply block 88. The mixed sample then is fed through a small intro tube 90 into the inlet 92 of the flow cell 10. The flow cell 10 is provided with a pair of electrodes 94 and 96, disposed on opposite sides of the aperture or orifice 12, for purposes to be described shortly hereinafter. The aperture 12 and the flow cell 10 are as described with reference to FIG. 1. The flow cell 10 thus is capable of simultaneous electronic and optical cell analysis measurements, as will be described later on herein. The cells are hydrodynamically focused by a sheath fluid 98, while passing through the center of the aperture, by means well known in the art. The sample material and the sheath fluid flow out of the cell chamber via an exit port 99 and into a waste container 100.

The helium-neon (HeNe) laser 22 is of relatively low power, for example, 0.8 milliwatts, and is directed into the lens system 18. The lens system 18 comprises two cross-cylindrical lenses. The focal lengths of the lenses of the lens system have been designed to work together so as to create the beam of light 20 which is oblate or elongated so that the beam is stretched horizontally, as earlier described herein. This optical arrangement permits minor deviations of the optical path without disturbing the optical output.

An electrical source unit 102 provides electrical current source, detection, and amplification means for RF and DC. Radio-frequency current from an oscillator-detector 101 and direct current from a DC source 103 are summed within a coupling circuit 105 and fed to electrodes 94, 96 over a line 111 establishing current flow through the aperture 12. A particle or cell traversing the aperture 12 momentarily changes the impedance of the aperture 12, modulating the RF and DC components of the current through the aperture. The RF current modulation caused by this impedance change is filtered and fed through the coupling circuit 105, to the oscillator-detector 101, which provides a detected pulse to a RF preamplifier 107, which outputs a "RF pulse" 118. Concurrently, the modulation to the direct current caused by the impedance change is filtered and fed through the coupling circuit 105, to a DC preamplifier 109, and output as "DC pulse" 116. The above description of electrical source unit 102 is a preferred form which is described fully in pending U.S. patent application Ser. No. 06/921,654, filed Oct. 21, 1986, to Wallace H. Coulter et al., entitled "Particle Analyzer for Measuring the Resistance and Reactance of a Particle", and assigned to the Assignee of the present application, Coulter Electronics, Inc. This electrical source unit 102 can consist of any other design that is capable of yielding the same results. Some embodiments of this invention utilize only DC and not RF; thus, in those cases, the electrical source unit 102 will contain only the DC source 103 and the DC preamplifier 109.

In FIG. 5, the light scatter photodetector assembly 24 is shown centered about the laser light axis 26, with the mask 28 and the beam dump 30, to remove both laser noise as well as low angle forward light scatter, scattered light below 10°, relative to the laser axis, as described in one or more of FIGS. 1 through 4. The photodetector assembly 24 collects and transduces the MALS or an annular light collection range of 10° to 70°, which signal is provided in the form of pulses, representative of the particles or cells traversing the laser beam 20 in the aperture 12, these pulses being the output of preamplifier 104.

As shown in FIG. 5A, three electrical outputs are generated by the electro-optical system, namely, DC, RF, and MALS as the electrical pulses 116, 118, and 120. These pulses are fed to respective amplifiers 124, 122, and 126, which latter members contain filtering and pulse shaping circuits, such as DC restoration. The amplifier outputs next are fed to respective peak detector circuits 130, 128, and 132 where the respective signals are peak sensed and the voltages of each of the peaks then is fed to respective analog to digital convertors 134, 136, and 138. The amplifier 126 provides a logarithmic response, so that the output of pulse peak detector circuit 132 is proportional to the log of MALS.

The outputs from the analog to digital convertors are passed to a data processing unit 140, for example, an IBM PC, for further processing, as will be described shortly. A strip or ticket printer 142 can be coupled to one of the data processing output 144, and a second output 146 can feed information from the host processor 140 to a graphics printer 148. A visual monitor 150, such as a CRT, can be provided for instantaneous review of the status of the data being processed by the host apparatus 140.

A divider circuit 154, of which there are commercially available units, is coupled to receive the DC peak pulse and the RF peak pulse, with the DC output being fed to the denominator of the divider 154 and the RF output being fed to the numerator of the divider 154. The output line 160 of the divider 154 circuit thus provides a signal characterized as "opacity", which is coupled to an A/D convertor 172.

A function circuit 161, detailed in FIG. 5B, generates "rotated light scatter" or RLS 170. Referring to FIG. 5B, a DC peak detector output 152 is connected to an attenuator 155, which has an attenuation factor of K. The attenuated DC then is connected to one node of a summing circuit 166. A constant offset voltage V2 153 is applied to the other node of the summing circuit 166 with its output being applied to the denominator input of an analog divider 162. A log of light scatter, LLS, output 164 is fed to one node of a summing circuit 168. A constant offset voltage V1 165 is applied to the other input node of the summing circuit 168, with its output being applied to the numerator input of the analog divider 162. The output 170 of the function circuit 161 is defined as: RLS=(LLS+V1)/[(DC/K)+V2]. For example, assuming that the range of the outputs of the peak detectors is from 0 to +10 volts, K is set to an attenuation factor of 5, V1 is set to −4.83 volts and V2 is set to +4.0 volts. The output 170 of analog divider 162 is defined to be full scale, or +10 volts, when its two inputs have a ratio of one. The RLS output 170 is applied to an analog to digital convertor 174. Alternatively, the RLS parameter can be derived by means of a digital logic circuit.

The circuit arrangement of FIGS. 5, 5A, and 5B provides three raw parameters DC, RF, and light scatter, as well as two computed, rotated, or derived parameters, namely, "opacity" and "rotated light scatter". This enables the system of the preferred embodiment to examine five discrete particle populations, as will be described subsequently herein.

The five main signals: RF, opacity, DC, RLS, and MALS are fed to an oscilloscope switching control and population discrimination circuit 180 from which a signal is fed to the X and Y axes 182 and 184 of a data display oscilloscope 186. A brightening pulse 178 also is fed to the oscilloscope 186 each time cell data is present. The data display oscilloscope can display data from any two parameters on a real time basis. Within the circuit 180, analog comparators perform a gating function on the data represented by the values of these pulses and then increment one of five counters 188, 190, 192, 194, and 196 representative of subpopulations identified as neutrophils, eosinophils, basophils, lymphocytes, and monocytes, respectively. Thus, depending on the cell type, an individual counter is incremented, while the graphics printer 148 or ticket printer 142 can produce histograms and matrices of the actual cell subpopulations for visible study and/or diagnosis.

As earlier mentioned herein, the present system is capable also of producing useful data and information regarding subpopulations of biological cells, without the employment of a Coulter type aperture or the utilization of Coulter DC or RF signal processing.

Figure 6C:
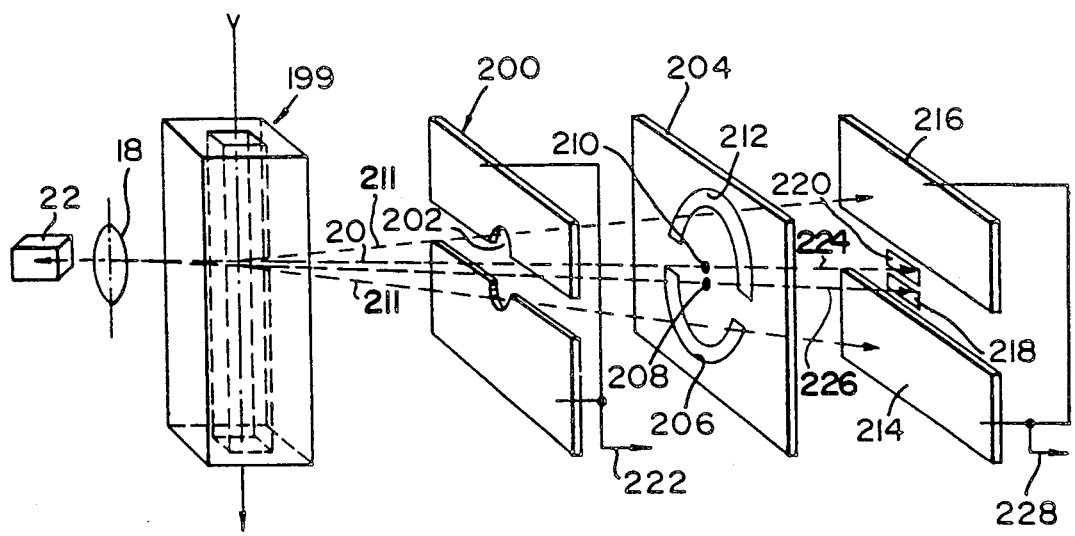
FIG. 6C is an exploded side view (not to scale) of a modified flow cell without a Coulter type sensing aperture.
Figure 6:
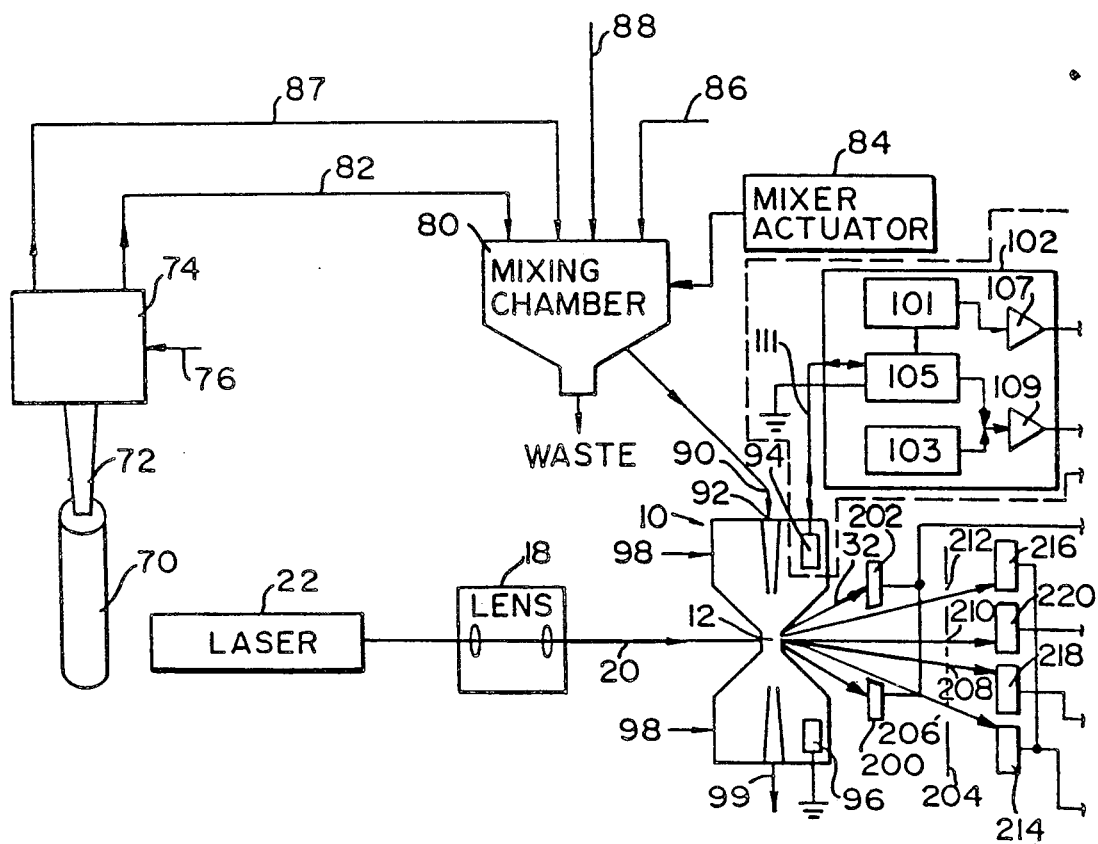
FIGS. 6, 6A, and 6B taken together constitute a block diagram of a modified version of the circuit of FIGS. 5, 5A, and 5B utilizing an optical flow chamber.
Figure 6A:
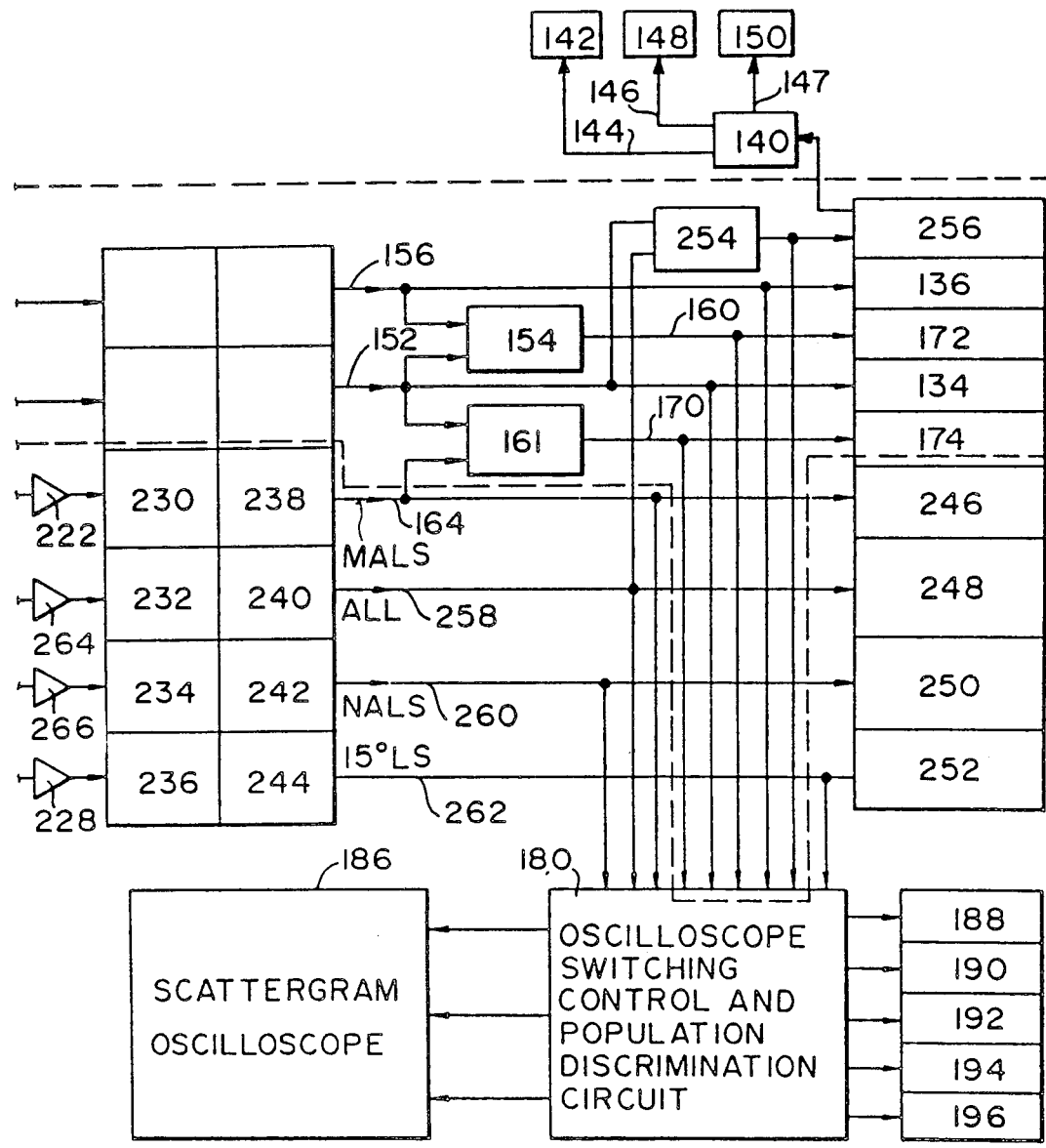

The system illustrated in FIGS. 6 and 6A employs the same sample intake and/or preparation as previously described for FIGS. 5, 5A, and 5B. Each of the components to the left of flow cell 10 is identical with these same components in FIGS. 5, 5A, and 5B and bear the same reference character designations.

Figure 6B:
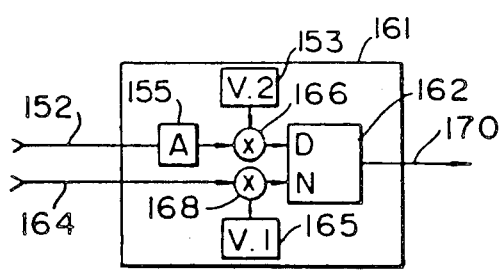

In the purely optical version of FIGS. 6, 6A and 6B, the section enclosed by dashed lines, containing the components associated with sensing and processing the electrical parameters DC and RF, is not included. The structure shown in the exploded view of FIG. 6C illustrates a flow cell 199, which does not require a Coulter type sensing aperture 12 and its associated electrodes 94, 96 for electrical (DC and RF) sensing, and can consist of a long, uniform, square, quartz channel of 250 micrometer internal cross section, an example of which is employed in the COULTER® EPICS® C as the Biohazard Flow Cell.

Arranged outboard of the flow chamber 199, to the right in FIG. 6, is a MALS sensor 200 which can be fabricated as a two-part assembly as shown, or it can be a single, unitary structure provided with a central axial opening or aperture 202.

Optically downstream of the sensor assembly 200 is a mask 204, which can be a unitary piece of hardware, that is provided with a plurality of light apertures 206, 208, 210, and 212. The apertures 206 and 212 are arranged at an angle of 15°±5° and provide for 15° LS. Light rays 211 are illustrated impinging on photodetectors 214 and 216. The aperture 208 is disposed off axis at approximately 0.5° to 2° and permits the pickup of narrow angle light scatter (NALS) information. Light ray 226 is illustrated impinging on photodetector 218. The aperture 210 is disposed on axis with respect to the laser beam 20 and provides axial light loss (ALL) information. Light ray 224 is illustrated impinging on photodetector 220. Immediately behind the mask 204 are located light scatter signal photodetectors 214, 216, 218, and 220 for the production of signal information relating to 15° light scatter, narrow angle light scatter, and axial light loss, respectively. Since the electrical signal output developed by each of the light scatter sensors 200, 214, 216, 218 and 220 is relatively low, a separate preamplifier 222, 264, 266, and 228 is provided for each output signal, with outputs of the detectors 214 and 216 being summed by the preamplifier 228. The preamplified signals then are amplified in respective amplifiers 230, 232, 234, and 236 and then fed to individual peak detectors 238, 240, 242, and 244. With the voltage value of each of the signal pulses present at the outputs of the peak detectors, the respective output signals then are fed to respective A/D convertors 246, 248, 250, and 252 and thence to the data processor (CPU) 140 as in FIGS. 5, 5A, and 5B.

The oscilloscope switching control and population discrimination circuit 180 functions as earlier described, but utilizes only the MALS signal, the ALL signal, the NALS signal, and the 15° LS signals to produce the histogram and matrices, to be described.

In another version, all sections of FIG. 6 and 6A are employed. Electrical RF and DC, and optical MALS, ALL, NALS, and 15° LS parameters are as previously described. An additional analog divider 254 is employed, with the ALL output signal fed to the numerator input and the DC output signal fed to the denominator input of the divider 254. The resulting ALL/DC signal then is fed to an A/D convertor 256 and to the oscilloscope switching control and population discrimination circuit 180, as earlier described.

ALL data, as obtained in the instrument just described, provides a measurement of relative cell size which approximates that obtained with electronic cell volume, or Coulter volume, referred to as Coulter DC or DC in this invention. Computing the division of ALL/DC yields a new parameter which is helpful in classifying certain cell populations, as will be shown.

FIGS. 7 through 27 are data representations of the information developed by different embodiments of the present system utilizing whole blood, native white cell populations, and subpopulations.

The following paragraphs refer to the system block diagram shown in FIGS. 5 and 5A, in which cells are classified by their responses to DC, RF, and MALS.

Figure 7:
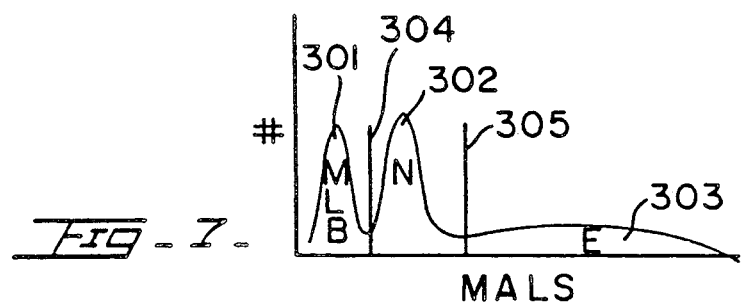
FIGS. 7 through 27 are histograms and scattergrams illustrating and explaining the results of the methodology and apparatus of the present invention.
Figure 8:
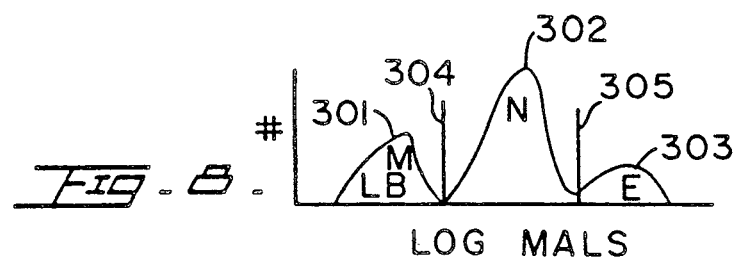

FIG. 7 is a histogram of the MALS output of the device of FIG. 1, as provided by the electro-optical system of FIG. 5. The same data is shown in FIG. 8, which is a representation of a histogram of the log of MALS. Both FIGS. 7 and 8 show three populations or peaks which classify leukocytes into three groups: lymphocytes, monocytes, and basophils 301; neutrophils 302; and eosinophils 303. Solid vertical lines 304 and 305 represent valleys separating these three peaks.

Figure 9:
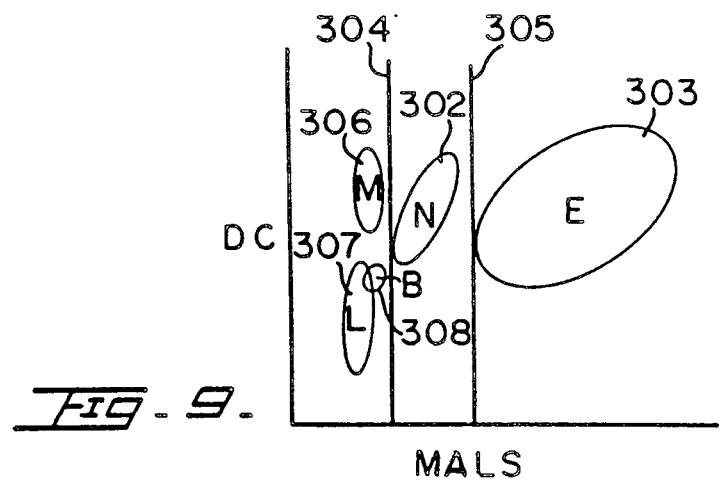
Figures 10, 11:
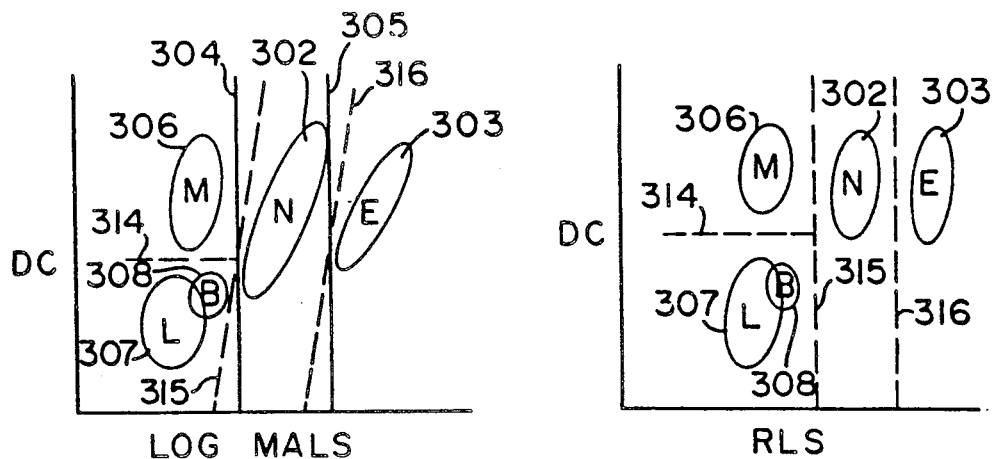

FIG. 9 is characterized as a matrix, illustrating MALS data versus or compared to DC data. FIG. 10 shows a matrix of log MALS versus DC. In both cases, the data contains the same information, with only a difference in scale. Five leukocyte populations are discerned: neutrophils 302, eosinophils 303, monocytes 306, lymphocytes 307, and basophils 308. The two solid lines 304 and 305 correspond to the vertical lines in FIGS. 7 and 8.

Figure 12:
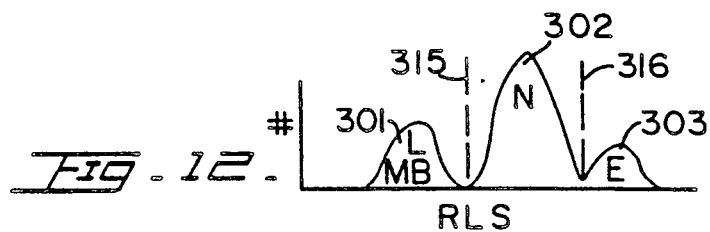

FIG. 12 shows a histogram of RLS, which is obtained by dividing the log of MALS by DC. Its data corresponds to that of FIGS. 7 and 8. FIG. 11 shows a matrix of RLS versus DC, and its data corresponds to that of FIGS. 9 and 10. Rotating the MALS data provides better separation between the three peaks 301, 302, and 303, as seen in FIG. 12. Dashed lines 315 and 316, shown on FIGS. 11 and 12, describe improved lines of separation between populations and are also shown in FIG. 10 to help to illustrate the ratio function.

Figure 13:
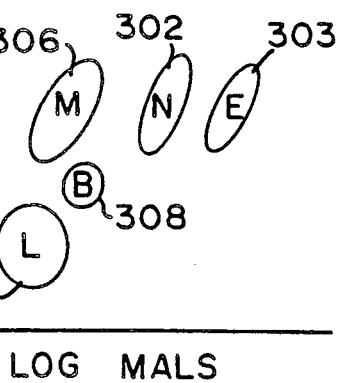

FIG. 13 shows a matrix of log MALS versus RF. Five populations of leukocytes can be distinguished and they are the same as those shown in FIGS. 9, 10, and 11 with one major difference, the basophils 308 are better separated from the lymphocytes 307 than in FIGS. 9, 10, and 11.

Figure 14:
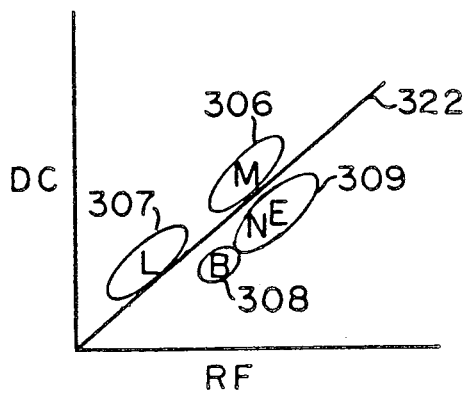

FIG. 14 shows a matrix of RF versus DC. Four leukocyte populations are discerned: monocytes 306, lymphocytes 307, basophils 308, and a cluster or group composed of neutrophils and eosinophils 309. Since DC measures cell volume and the RF measurement is highly correlated to DC, dividing RF by DC yields opacity, which is independent of volume and related to cell internal conductivity.

Figure 15:
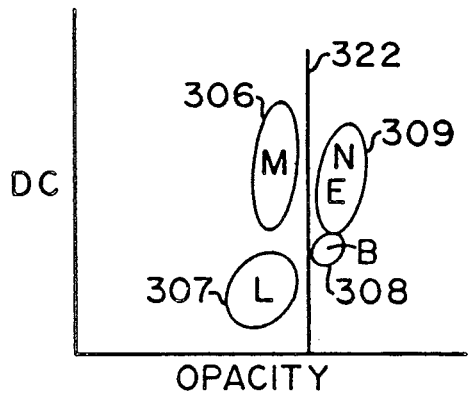

FIG. 15 shows a matrix of opacity versus DC, which contains the same four populations shown in FIG. 14, but is on a different scale. It is of particular interest that the populations can be divided into two groups by opacity thereby clarifying the presentation, as shown by line 322 in FIG. 15, while the same separation cannot be achieved by RF or DC alone, as shown in FIG. 14, with iso-opacity line 322 plotted diagonally. The utility of line 322 now will be explained.

Figure 16:
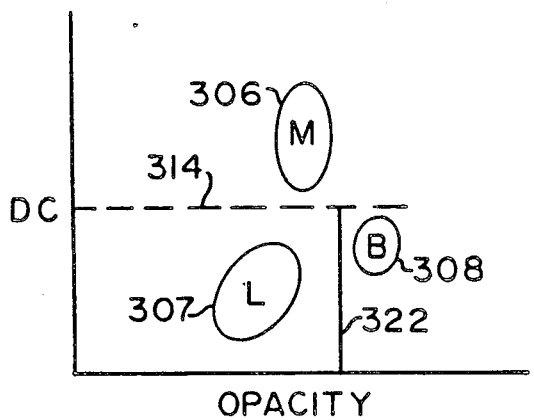
Figure 17:
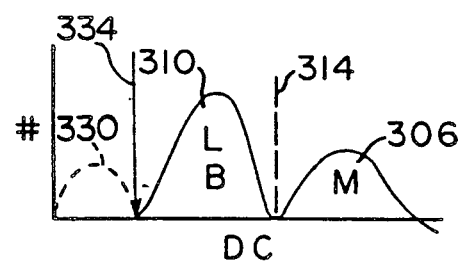

Gating on RLS for values less than those indicated by line 315 in FIG. 12 and generating a matrix of opacity versus DC will yield the data shown in FIG. 16. Only those leukocyte populations that showed on the left of line 315 on FIG. 12 are present in FIG. 16: monocytes 306, lymphocytes 307, and basophils 308. A horizontal dashed line 314 separates the monocytes 306 from the other two populations 307-308. A solid line 322 separates the lymphocytes 307 from the basophils 308. Following is a method for obtaining lines 314 and 322. In FIG. 17, a histogram of DC for the data of FIG. 16 shows two peaks containing two groups: monocytes 306 and the cluster 310 of lymphocytes and basophils. This data is obtained by gating on RLS for values less than those indicated by the line 315 in FIG. 12 and generating a matrix of opacity versus DC. The valley between these two peaks is identified by the dashed line 314 in FIG. 17. The line 314 also is shown in FIGS. 10, 11, and 16. In FIG. 17, the peak 330, corresponding to abnormal, low volume lymphocytes, may be found to the left of the lymphocyte plus basophil peak 310, and is separated by line 334.

Figure 18:
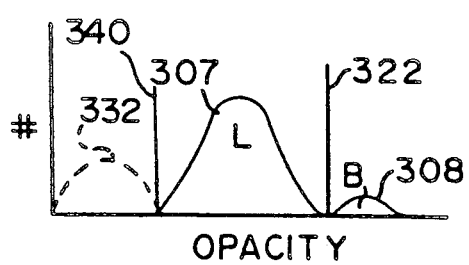

Referring back to FIG. 11, gating on RLS for values less than line 315 and also gating on DC for values less than line 314, and generating a histogram of opacity will yield FIG. 18, which shows two peaks: lymphocytes 307 and basophils 308, with line 322 separating them. A third peak 332, representing abnormal, low opacity lymphocytes, may be found to the left of normal lymphocytes 307 and separated by line 340.

Figure 19:
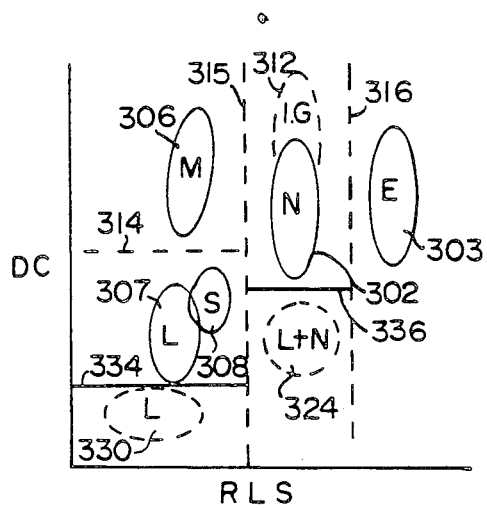

FIG. 19 shows a matrix of RLS versus DC for all leukocytes. It contains all the populations shown in FIG. 11, but contains extra leukocyte populations that are present only in abnormal cases: immature granulocytes 312, which are partially overlapping with neutrophils 302; low volume lymphocytes 330, separated from normal lymphocytes 307 by line 334; and a population or cluster 324, which can be composed of high light scatter lymphocytes, damaged neutrophils, or both of these cell types, and which is separated from normal neutrophils 302 by line 336.

Figure 20:
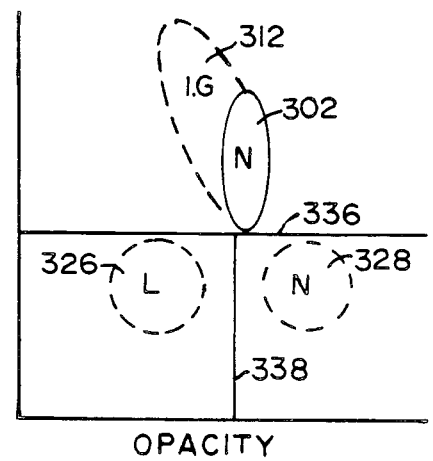

Generating a matrix of opacity versus DC, while gating on RLS between the value of lines 315 and 316, as in FIG. 19, will yield the following populations, shown in FIG. 20: normal, mature neutrophils 302; immature granulocytes 312; high light scatter lymphocytes 326; and damaged neutrophils 328. The last two populations, which are both separated from normal neutrophils 302 by line 336, and which are separated from each other by line 338, appear as one population 324 in FIG. 19.

Figure 24:
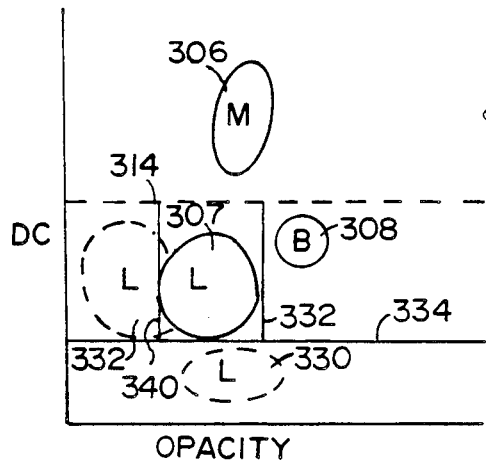

FIG. 24 shows a matrix of opacity versus DC, while gating on RLS for values less than line 315, as shown in FIG. 19. Shown in solid outline are normal populations: lymphocytes 307, basophils 308, and monocytes 306, which are separated from the first two populations by dashed line 314. This data is equivalent to the data shown in FIG. 16. Shown in dashed lines are two abnormal populations: low volume lymphocytes 330, which are separated from all other populations by line 334; and low opacity lymphocytes 332, which overlap completely with normal lymphocytes 307 on FIG. 19.

From the previous description of the data shown in FIGS. 7 through 19, obtained by means of the apparatus embodiment shown in FIGS. 5, and 5A, a method for classifying leukocytes into at least five populations by using DC, RF, and MALS, is next described:

1. Generate a histogram of RLS, FIG. 12, and find lines of separation 315 and 316. Count neutrophils 302 and eosinophils 303.
2. Gate on RLS for values less than line 315; generate a DC histogram, FIG. 17, and find the line of separation 314. Count monocytes 306. Find low volume line of separation 334 and count abnormal low volume lymphocytes 330, if present.
3. Gate on RLS for values less than line 315 in FIG. 12 and gate on DC for values between lines 334 and 314 as shown in FIG. 17; then generate the opacity histogram FIG. 18. Find the line of separation 322 and count lymphocytes 307 and basophils 308. Find line 340 and count abnormal low opacity lymphocytes 332, if present. Alternatively, fit a gaussian or normal distribution curve to the lymphocyte peak 307; remove the peak 307; count lymphocytes 307, basophils 308, and low opacity lymphocytes 332.
4. Gate on RLS for values between 315 and 316 of FIG. 19; generate DC histogram, not shown; find line 336 that separates normal neutrophils 302 from other abnormal populations 324, as shown in FIG. 19.
5. Gate on RLS for values between lines 315 and 316, and on DC for values greater than line 336 of FIG. 19; generate an opacity histogram, not shown; identify normal neutrophils peak 302 and count abnormal immature granulocytes 312 to the left, as shown in FIG. 20.
6. Gate on RLS for values between lines 315 and 316, and on DC for values less than line 336 of FIG. 19; generate an opacity histogram, not shown; find line 338 and count high light scatter lymphocytes 326 to the left and damaged neutrophils 328 to the right, as shown in FIG. 20.

Another embodiment of FIGS. 5, 5A, and 5B uses MALS, DC, and RLS. In that case, electrical source unit 102 will consist only of the DC source 103 and the DC preamplifier 109. The oscillator-detector 101, RF preamplifier 107, coupling circuit 105, amplifier 122, peak detector 128, divider circuit 154, analog to digital convertors 136 and 172 are related to RF and thus are not used. FIG. 11 shows a matrix of RLS versus DC, with five leukocyte populations, as previously described. A method for classifying said leukocytes into at least five populations, using DC and MALS, next is described:

1. Generate a histogram of RLS, FIG. 12, and find the lines of separation 315 and 316. Count neutrophils 302 and eosinophils 303.
2. Gate on RLS for values less than the line 315, generate a DC histogram, FIG. 17, and find the line of separation 314. Count monocytes 306.
3. Gate on RLS for values less than line 315 and gate on DC for values less than the line 314, and generate an RLS histogram (not shown). Identify and count lymphocytes and basophils.

In yet another embodiment of FIGS. 5, 5A, and 5B only RF and MALS are used. In that case, all DC-related components: DC source 103, DC preamplifier 109, amplifier 124, peak detector 130, divider circuit 156, analog function circuit 151, and analog to digital convertors 134, 172, 174 are omitted. The log MALS versus RF matrix in FIG. 13 shows five leukocyte populations: lymphocytes 307, basophils 308, monocytes 306, neutrophils 302, and eosinophils 303.

The following paragraphs refer to the system block diagram described in the first version of FIG. 6, which relates to a flow cytometer system consisting only of optical measurements and not requiring DC or RF measurements, nor a Coulter type aperture, components enclosed by dashed lines not being included.

In an embodiment of FIGS. 6, 6A, and 6B employing only narrow angle light scatter and log of MALS, it is possible to obtain a four population leukocyte differential count.

Figure 21:
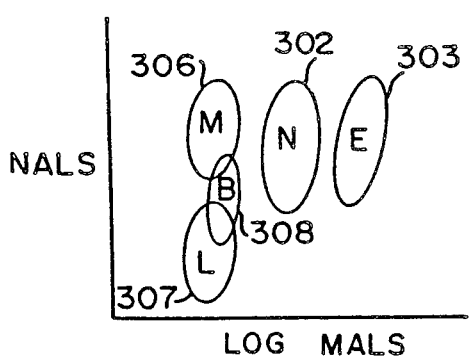

Referring to FIG. 21, a matrix of log MALS versus narrow angle light scatter, NALS, shows clearly four populations: lymphocytes 307, monocytes 306, neutrophils 302, and eosinophils 303; with a fifth population, basophils 308, overlapping with the lymphocytes 307 and monocytes 306.

Figure 22:
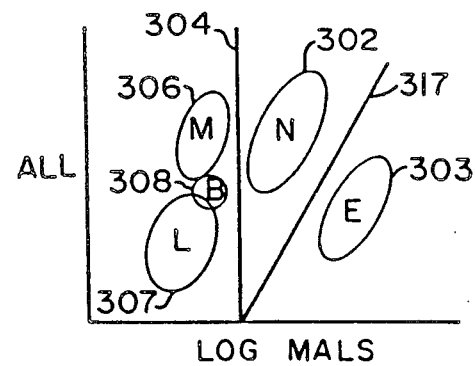

In another embodiment of FIGS. 6, 6A, and 6B employing only MALS and axial light loss, generating a matrix of log MALS versus ALL, shown in FIG. 22, five leukocyte populations can be distinguished: lymphocytes 307, basophils 308, monocytes 306, neutrophils 302, and eosinophils 303. Gating lines 304 and 317 can be employed to differentiate the neutrophils 302 from the other cell types. Line 317 can be found by a rotation of data based on dividing the log MALS by ALL.

Figure 23:
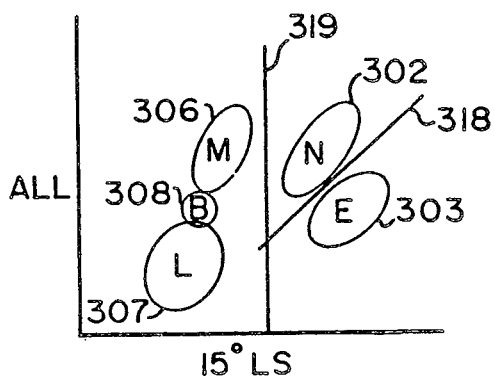

In yet another embodiment of FIGS. 6, 6A, and 6B employing only 15° LS and ALL, the representation of FIG. 23 is produced.

FIG. 23 shows a matrix of 15° LS versus ALL. Five leukocyte populations are detected and the patterns appear similar to those of FIG. 22, with one exception: the separation between the neutrophils 302 and the eosinophils 303 on FIG. 23 is not as good as in FIG. 22. Neither 15° LS nor ALL can by itself differentiate between the neutrophils 302 and the eosinophils 303. A combination of both measurements is required. The best line 318 of gating or separation is a diagonal line, obtained by dividing 15° LS by ALL. A gating line 319 provides separation between the neutrophils 302 and the three other cell populations 306, 307, and 308, and is analogous to the line 304 on MALS or log MALS.

The following paragraphs describe data obtained with the complete system shown in FIG. 6, 6A, and 6B.

In a system such as shown in FIGS. 6, 6A, employing at least DC, MALS, and ALL, a method for classifying leukocytes into five populations is described with reference to FIGS. 11, 25, 26, and 27.

Figure 25:
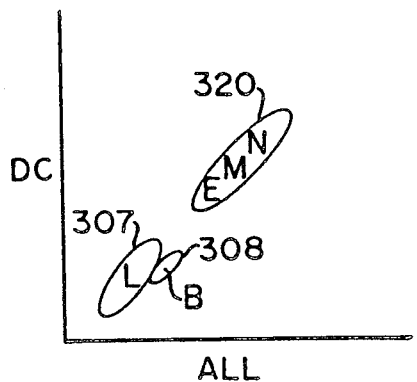

FIG. 25 shows a matrix of ALL versus DC. Since ALL has very high correlation with DC, only three leukocyte populations can be discerned: lymphocytes 307, basophils 308, and the overlapped monocytes, neutrophils, and eosinophils 320. A ratio of these two measurements yields an independent parameter.

Figure 26:
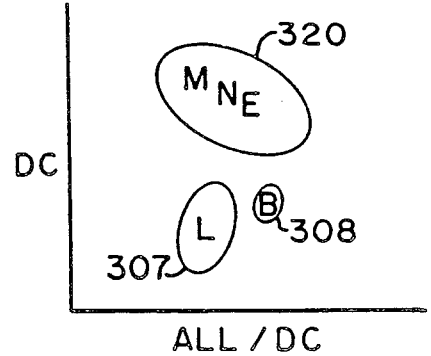
Figure 27:
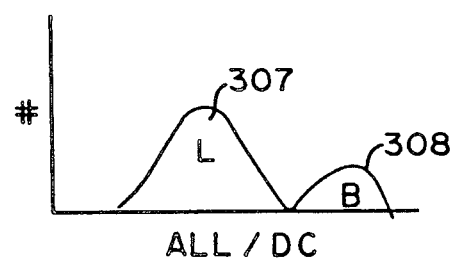

FIG. 26 shows a matrix of ALL/DC versus DC and shows the same populations just described, but rotated to produce greater separation, especially between the lymphocytes 307 and the basophils 308.

As previously described, the neutrophils 302 and the eosinophils 303 can be identified and enumerated by RLS versus DC, see FIG. 11. A DC histogram, shown in FIG. 17, is generated by gating on RLS for values less than line 315, shown in FIG. 11. On this DC histogram, a cluster 310 containing lymphocytes and basophils is separated from monocytes 306, by a line 314. Monocytes are counted. Finally, by gating both on RLS for values less than the line 315 and on DC for values less than the line 314, as shown in FIG. 11, a histogram of ALL/DC, shown in FIG. 27, yields two populations: lymphocytes 307 and basophils 308.

There thus has been described a new, novel, and unobvious technique and apparatus for providing both a solely optical as well as an electro-optical apparatus for providing at least a five part differential analysis of biological cell populations and displaying data corresponding to such populations as histograms and matrices for diagnostic purposes.

It is to be understood that the illustrative embodiments set forth herein constitute examples of the principles of the present invention, but that numerous alternatives will occur to those of ordinary skill in the art, without departure from the scope of this invention.

What we claim is:

1. Apparatus for selectively differentiating at least one white blood cell subpopulation in a blood sample, whereby differentiation is based upon individual cell light scatter, said apparatus comprising:

a cytometric flow cell including inlet and outlet means for the ingress and egress of a blood sample in liquid suspension;

introducing means for introducing a blood sample including white cells into said flow cell inlet to cause said white cells to flow through said flow cell;

a beam of light arranged such that the axis of its light rays pass through said flow cell at right angles to said flow of white cells;

extinguishing means, axially aligned with said axis of light rays, for extinguishing the light rays which are at a low angle to said beam axis which are scattered by the white cells in response to the impingement of light thereon as they pass through said beam;

light collection means responsive to the light scattered by said cells in a median angle (MALS) greater than 10°, but less than 70°, relative to said axis after passing through said beam for producing median angle output signal data, eosinophil subpopulation data being generated by and derived from the scattered rays in the (MALS) range of 20° to 70°;

utilizing means for utilizing said output signal data from said light collection means for utilizing the portion of said (MALS) in the range of 20° to 70° to differentiate the eosinophil subpopulation; and said apparatus is constructed to operate to differentiate white blood cells, especially including eosinophil blood cells, as a result of the inherent, natural characteristics of the white blood cells and without treatment of any kind for specifically altering the inherent, natural characteristics of the white blood cells for differentiating eosinophils.

2. Apparatus in accordance with claim 1 wherein said means for extinguishing said small angle light rays comprises a horizontally disposed light interrupting means is positioned to intercept and block all but the scattered light rays in the range of 20° to 60°.

3. Apparatus in accordance with claim 1 wherein said extinguishing means for selectively occluding said light rays includes angularly disposed apertures therein permitting the passage of said light rays at prescribed angles prior to impingement upon said light collection means.

4. Apparatus in accordance with claim 3 wherein at least one of said apertures is located on the axis of said light rays leaving said flow cell.

5. Apparatus in accordance with claim 1 wherein said light collection means includes means disposed on said light beam axis responsive to axial light loss.

6. Apparatus in accordance with claim 1 in which said light collection means comprises individual members disposed at 45° relative the axis of said light beam.

7. Apparatus in accordance with claim 1 wherein said flow cell is circular in cross section.

8. Apparatus in accordance with claim 1 wherein said flow cell is square in cross section intermediate said inlet and outlet.

9. Apparatus in accordance with claim 1 wherein said light collection means is disposed adjacent to at least three sides of said flow cell.

10. Apparatus in accordance with claim 1 wherein said light collection means is constructed and arranged with respect to construction and arrangement of said light extinguishing means to collect and respond to light scattered by said sample in the angular range of 20° to 70° relative to the axis of the light leaving said flow cell aperture.

11. Apparatus in accordance with claim 1 further including first electronic circuit means for generating: a first signal of Coulter DC volume; said first electronic circuit means employs said output signal from said light collection means (MALS) in the range of 10°-70° for generating a second signal of log of median angle light scatter (log of MALS); and a first output is developed from said first and second signals as rotated light scatter (RLS).

12. Apparatus in accordance with claim 11 including second electronic circuit means for generating: a third signal of Coulter RF, and generating a second output of Coulter opacity, which is produced by and results from said first signal of Coulter DC volume and said third signal of Coulter RF.

13. Apparatus according to claim 12 constructed and arranged such that: said first output of RLS yields data specific to the white cell subpopulation of neutrophils, separate from the eosinophils, and also a group of three subpopulations of lymphocytes, monocytes, and basophils; said first signal of Coulter DC volume yields data which separates the monocytes from said group of three subpopulations; and said second output of Coulter opacity yields data which separates the lymphocytes and basophils from said group of three subpopulations; whereby said apparatus differentiates the five white cell subpopulations of: eosinophils, neutrophils, monocytes, lymphocytes, and basophils.

14. Apparatus in accordance with claim 1 including first electronic circuit means for generating: a first signal of Coulter RF; and generating a second signal which employs said output signal from said light collection means (MALS) for producing log of median angle light scatter (log of MALS); and second electronic circuit means for comparing said first signal of Coulter RF and said second signal of log of MALS whereby five subpopulations of white blood cells can be differentiated.

15. A method for differentiating at least one white blood cell subpopulation in a blood sample, whereby differentiation is based upon individual cell light scatter, said method comprising the steps of: passing a beam of light along an axis and orthogonally through a fluid passageway while simultaneously flowing said blood sample through said passageway; extinguishing the rays of light which are at a low angel to said axis which are scattered by the white cells in response to impingement of light thereon as they pass through said beam of light; collecting the light scattered by said cells in a median angle (MALS) greater than 10°, but less than 70°, relative to said axis after passing through said beam of light; sensing the rays of light scattered in said median angle by each cell of said blood sample for producing median angle output signal data; said step of sensing providing signal data which is a result of the inherent, natural light scatter characteristics of the white blood cells without treatment of any kind for specifically altering the inherent, natural characteristics of said white blood cells for differentiating eosinophils, eosinophil data being contributed by the portion of (MALS) from 20° to 70°; and utilizing said portion of said median angle light scatter signal data to differentiate the eosinophil subpopulation.

16. The method of claim 15 in which said step of flowing includes the steps of providing said fluid passageway within a Coulter volume fluid flow chamber, hydrodynamically focussing said blood sample as it is flowing through said chamber, generating Coulter volume DC signal information (DC), comparing said DC with signal information obtained from the light scatter sensing, whereby said processing produces data which differentiates five distinct white cell subpopulations, namely: eosinophils, neutrophils, monocytes, lymphocytes and basophils.

17. The method of claim 15 including the additional processing step of developing a log of median angle light scatter signal information (log of MALS) from said MALS for classifying said white blood cells into three distinct groups, namely: eosinophils, neutrophils, and lymphocytes, monocytes and basophils.

18. The method of claim 17 including the steps of generating Coulter volume DC signal information (DC) and dividing the log of MALS by said DC for generating rotated light scatter signal information (RLS).

19. The method of claim 18 including the step of comparing said RLS with said DC, whereby said processing produces data for differentiating at least five white blood cell subpopulations, namely: eosinophils, neutrophils, lymphocytes, monocytes and basophils.

20. The method of claim 18 wherein RLS is analyzed in a histogram providing signal information to yield three separate populations: eosinophils, neutrophils, and a combination population including lymphocytes, monocytes and basophils.

21. The method of claim 20 including the steps of gating on the RLS data to produce a DC histogram separated so as to provide up to at least three separate populations: monocytes, a mixture of lymphocytes and basophils, and low volume lymphocytes.

22. The method of claim 21 further including the steps of generating a Coulter RF signal value information (RF), dividing said RF by said DC to produce an opacity signal, and including the further step of gating on the DC signal information to produce an opacity histogram separated so as to provide up to at least three separate populations: basophils, lymphocytes, and low opacity lymphocytes.

23. The method of claim 20 including the steps of gating on the RLS signal information to produce a DC histogram containing at least a population of normal neutrophils and possibly including a second population of other cell types.

24. The method of claim 23 further including the steps of generating a Coulter RF signal value information (RF), dividing said RF by said DC to produce an opacity signal, and including the step of gating on the DC signal information to produce an opacity histogram of said other cell types which are classified as damaged neutrophils and lymphocytes.

25. The method of claim 17 including the steps of generating Coulter volume DC signal information (DC) and comparing said log of MALS with said DC, whereby said processing produces data for differentiating at least five white blood cell subpopulations, namely: eosinophils, neutrophils, lymphocytes, monocytes and basophils.

26. The method of claim 17 including the steps of generating a Coulter RF signal value information (RF) and comparing said log of MALS and said RF, whereby said processing produces data for differentiating five subpopulations of white blood cells, namely: eosinophils, neutrophils, monocytes, lymphocytes and basophils.

27. The method of claim 17 including the additional steps of obtaining narrow angle light scatter signal information (NALS) and thereafter comparing said log of MALS with said NALS, whereby said processing produces data for differentiating four white blood cell subpopulations, namely: lymphocytes, monocytes, neutrophils and eosinophils.

28. The method of claim 17 including the additional sensing steps of obtaining axial light loss signal information (ALL) and comparing said log of MALS with said ALL, whereby said processing produces data for differentiating five white blood cell subpopulations, namely: eosinophils, neutrophils, monocytes, lymphocytes and basophils.

29. The method of claim 15 including the additional steps of obtaining 15° light scatter signal information (15° LS) and axial light loss signal information (ALL), and comparing said 15° LS with said ALL, whereby said processing produces data for differentiating five subpopulations of white blood cells, namely: eosinophils, neutrophils, monocytes, lymphocytes and basophils.

30. The method of claim 15 including the additional steps of obtaining axial light loss signal information (ALL), generating Coulter volume DC signal information (DC), and comparing said ALL with said DC for producing data for differentiating three white blood cell subpopulations, namely: lymphocytes, basophils and eosinophils, monocytes and neutrophils.

31. The method of claim 15 including the steps of applying simultaneously to said flow cell passageway a Coulter volume DC signal (DC) and a Coulter RF signal (RF), and comparing said DC to said RF, whereby said processing provides data for differentiating an additional four white blood cell subpopulations, namely: neutrophils, monocytes, lymphocytes and basophils.

32. The method of claim 31 including the steps of electronically dividing said RF by said DC to produce an opacity signal which is independent of blood cell volume and is related to blood cell internal conductivity, and comparing said opacity signal to said DC, whereby said processing provides data for enhancing the differentiating of said four white blood cell subpopulations.

33. The method of claim 15 including the step of conditioning said white blood cells such that they approximate native state as a result of the inherent, natural characteristics of the whole blood cell and not as a result of a treatment for specifically altering the characteristics of said. whole blood cells for differentiating eosinophils while said cells are flowing through said passageway.

34. A method for differentiating at least one white blood cell subpopulation in a blood sample, whereby differentiation is based upon individual cell light scatter, said method comprising the steps of: passing rays of light along an axis and orthogonally through a fluid passageway while simultaneously flowing said blood sample through said passageway; extinguishing the rays of light which are at a low angle to said axis which are scattered by the white cells in response to impingement of light therein as they pass through said beam of light; collecting the light scattered by said cells in a median angle (MALS) greater than 10°, but less than 70°, relative to said axis after passing through said beam of light; sensing the rays of light scattered in said median angle for producing median angle output signal data by each cell of said blood sample; eosinophil subpopulation data being generated by and derived from the scattered rays in the (MALS) range of 20° to 70°; said step of sensing providing signal data as a result of the inherent, natural light scatter characteristics of the white blood cells without treatment of any kind for specifically altering the inherent, natural characteristics of said white blood cells for differentiating white blood cell subpopulations; and processing said output signal data to produce data for utilizing the portion of said (MALS) in the range of 20° to 70° to differentiate at least three subpopulations, namely eosinophils, neutrophils, and lymphocytes, monocytes and basophils.

35. A method for differentiating at least one white blood cell subpopulation in a blood sample, whereby differentiation is based upon individual cell light scatter, said method comprising the steps of: passing rays of light along an axis and orthogonally through a fluid passageway while simultaneously flowing said blood sample through said passageway; extinguishing the rays of light which are at a low angle to said axis which are scattered by the white cells in response to impingement of light thereon as they pass through said beam of light; collecting the light scattered by said cells in a median angle (MALS) greater than 10°, but less than 70°, relative to said axis after passing through said beam of light; sensing the rays of light scattered in said median angle by each cell of said blood sample for producing median angle output signal data; said step of sensing provides signal data as a result of the inherent, natural light scatter characteristics of the white blood cells without treatment of any kind for specifically altering the inherent, natural characteristics of said white blood cells for differentiating white blood cell subpopulations and is within a collection angle of from 10° to 70° relative to said axis; processing electronically said output signal data to produce white blood cell differentiating data; wherein said step of sensing is operative with the untreated white blood cells and within a collection angle of from 10° to 70° relative to said axis; eosinophil subpopulation data being generated by and derived from the scattered rays in the (MALS) range of 20° to 70°; and including the additional steps of obtaining axial light loss signal information (ALL), generating Coulter volume DC signal information (DC), and comparing said ALL with said DC for producing data for differentiating three white blood cell subpopulations, namely: lymphocytes, basophils and eosinophils, monocytes and neutrophils.

36. The method of claim 35 including the further step of dividing said ALL by said DC, whereby said processing produces data for differentiating at least three white blood cell subpopulations, namely: lymphocytes, basophils and eosinophils, monocytes and neutrophils.

37. A method for differentiating at least one white blood cell subpopulation in a blood sample, whereby differentiation is based upon individual cell light scatter, said method comprising the steps of: passing rays of light along an axis and orthogonally through a fluid passageway while simultaneously flowing said blood sample through said passageway; extinguishing the rays of light which are at a low angle to said axis which are scattered by the white cells in response to impingement of light thereon as they pass through said beam of light; collecting the light scattered by said cells in a median angle (MALS) greater than 10°, but less than 70°, relative to said axis after passing through said beam of light; sensing the rays of light scattered in said median angle by each cell of said blood sample for producing median angle output signal data; said step of sensing providing signal data as a result of the inherent, natural light scatter characteristics of the white blood cells without treatment of any kind for specifically altering the inherent, natural characteristics of said white blood cells for differentiating white blood cell subpopulations; processing electronically the said output signal data to produce white blood cell differentiating data; wherein said step of sensing is operative with the untreated white blood cells and within a collection angle of from 10° to 70° relative to said axis; and including the steps of applying a DC and an RF current simultaneously to said flow cell passageway aperture producing a Coulter volume DC signal (DC) and a Coulter RF signal (RF), and comparing said DC to said RF, whereby said processing provides data for differentiating at least four white blood cell subpopulations, namely: neutrophils, monocytes, lymphocytes, and basophils.

38. A method for differentiating at least one white blood cell subpopulation in a blood sample, whereby differentiation is based upon individual cell light scatter, said method comprising the steps of: passing rays of light along an axis and orthogonally through a fluid passageway including a Coulter aperture while simultaneously flowing said blood sample through said passageway; sensing some of the rays of light scattered by each cell of said blood sample; processing electronically the results of said sensing step to produce white blood cell differentiating data; wherein said step of sensing provides median angle light scatter (MALS) signal data throughout a range of approximately 10°-70° and wherein said processing step develops a log of median angle light scatter signal (log of MALS); including the steps of applying a DC current simultaneously to said flow cell passageway aperture producing a Coulter volume DC signal (DC), dividing the log of MALS by said DC for generating rotated light scatter signal information (RLS) and comparing said DC with said RLS, whereby said processing provides data for differentiating and identifying at least four white blood cell subpopulations, namely: lymphocytes and basophils, monocytes, neutrophils, and eosinophils.

39. A method for differentiating at least one white blood cell subpopulation in a blood sample, whereby differentiation is based upon individual cell light scatter, said method comprising the steps of: passing rays of light along an axis and orthogonally through a fluid passageway including a Coulter aperture while simultaneously flowing said blood sample through said passageway, sensing some of the rays of light scattered by each cell of said blood sample; processing electronically the results of said sensing step to produce white blood cell differentiating data, wherein said step of sensing provided median angle light scatter (MALS) signal data throughout a range of approximately 10°-70° and said processing step develops a log of median angle light scatter signal (log of MALS), applying a DC and an RF current simultaneously to said flow cell passageway aperture for producing a Coulter volume DC signal (DC), dividing the log of MALS by said DC for generating rotated light scatter signal information (RLS), and comparing said DC with said RLS, whereby said processing provides data for differentiating and identifying at least four white blood cell subpopulations, namely: lymphocytes and basophils, monocytes, neutrophils, and eosinophils, dividing said RF by said DC for generating opacity signal information (OP), and comparing said DC with said OP while gating on said RLS, whereby said processing provides data for further differentiating and identifying one of said four white blood cell subpopulations into at least two white blood cell subpopulations, namely: lymphocytes and basophils.

40. A method for differentiating at least one white blood cell subpopulation in a blood sample, whereby differentiation is based upon individual cell light scatter, said method comprising the steps of: passing rays of light along an axis and orthogonally through a fluid passageway including a Coulter aperture while simultaneously flowing said blood sample through said passageway; sensing some of the rays of light scattered by each cell of said blood sample; processing electronically the results of said sensing step to produce white blood cell differentiating data; wherein said step of sensing provides median angle light scatter (MALS) signal data throughout a range of approximately 10°-70° and said processing step develops a log of median angle light scatter signal (log of MALS); applying a DC and an RF current simultaneously to said flow cell passageway aperture for producing a Coulter volume DC signal (DC), dividing the log of MALS by said DC for generating rotated light scatter signal information (RLS), dividing said RF by said DC for generating opacity signal information (OP), and comparing said DC with said RLS and said OP, whereby said processing provides data for differentiating and identifying at least five white blood cell populations, namely: lymphocytes, basophils, monocytes, neutrophils, and eosinophils.

* * * * *